(12) United States Patent
Wu et al.

(10) Patent No.: US 11,458,155 B1
(45) Date of Patent: Oct. 4, 2022

(54) ACTIVE INGREDIENT COMPLEXES, COMPOSITIONS AND METHODS FOR HANGOVER RELIEF AND TO AMELIORATE ALCOHOL-INDUCED LIVER DAMAGE

(71) Applicants: FULGENT LIFE INC., Irvine, CA (US); GUANG DONG HAI HE BIOTECHNOLOGY CO., LTD., Guang Dong (CN)

(72) Inventors: Yong Wu, Los Angeles, CA (US); Fei Zhou, Irvine, CA (US); Shengzhen Tang, La Verne, CA (US); Ke Wu, Downey, CA (US); Shiliu Tian, Downey, CA (US); Long Yi, GuangDong (CN)

(73) Assignees: FULGENT LIFE INC., Irvine, CA (US); GUANG DONG HAI HE BIOTECHNOLOGY CO., LTD., Guang Dong (CN)

( * ) Notice: Subject to any disclaimer, the term of this patent is extended or adjusted under 35 U.S.C. 154(b) by 0 days.

(21) Appl. No.: 17/527,629

(22) Filed: Nov. 16, 2021

(51) Int. Cl.
| | |
|---|---|
| *A23L 33/17* | (2016.01) |
| *A61K 31/7084* | (2006.01) |
| *A61K 31/198* | (2006.01) |
| *A23L 33/175* | (2016.01) |
| *A61K 31/375* | (2006.01) |
| *A23L 33/15* | (2016.01) |
| *A61K 31/353* | (2006.01) |

(52) U.S. Cl.
CPC .......... *A61K 31/7084* (2013.01); *A23L 33/15* (2016.08); *A23L 33/175* (2016.08); *A61K 31/198* (2013.01); *A61K 31/353* (2013.01); *A61K 31/375* (2013.01)

(58) Field of Classification Search
CPC ....................................................... A23L 33/17
See application file for complete search history.

(56) References Cited

U.S. PATENT DOCUMENTS

| | | |
|---|---|---|
| 2011/0280977 A1 | 11/2011 | Park et al. |
| 2016/0074445 A1 | 3/2016 | Smith et al. |
| 2016/0346266 A1 | 12/2016 | Tolleth et al. |

(Continued)

OTHER PUBLICATIONS

Shen et al., "Dihydromyricetin as a novel anti-alcohol intoxication medication," J Neurosci 32(1):390-401, 2012.*

(Continued)

*Primary Examiner* — Rosanne Kosson
(74) *Attorney, Agent, or Firm* — Lewis Roca Rothgerber Christie LLP

(57) ABSTRACT

An active ingredient complex is effective to treat, reduce the likelihood of developing, reduce the severity of, or ameliorate acute alcoholic liver damage or the symptoms of a hangover. In some embodiments, the active ingredient complex includes NADH (nicotinamide adenine dinucleotide (NAD)+hydrogen (H)), L-cysteine, dihydromyricetin (DHM), N-acetyl-cysteine (NAC), L-theanine, and buffered vitamin C, or pharmaceutically acceptable salts or derivative thereof. According to some embodiments, a pharmaceutical composition or dietary supplement may include the active ingredient complex and one or more pharmaceutically acceptable carriers, excipients, adjuvants and/or diluents.

20 Claims, 10 Drawing Sheets

(56) References Cited

U.S. PATENT DOCUMENTS

2019/0314298 A1 10/2019 Goyal et al.
2020/0215027 A1 7/2020 Prud'Homme et al.

OTHER PUBLICATIONS

Li et al., "The role of oxidative stress and antioxidants in liver diseases," Int J Mol Sci 16:26087-26124, 2015.*
Achari AE, Jain SK, "I-Cysteine supplementation increases insulin sensitivity mediated by upregulation of GSH and adiponectin in high glucose treated 3T3-L1 adipocytes," Arch Biochem Biophys 2017, 630:54-65.
Agarwal S, Fulgoni VL, 3rd, Lieberman HR: Assessing alcohol intake & its dose-dependent effects on liver enzymes by 24-h recall and questionnaire using NHANES 2001-2010 data. Nutr J 2016, 15(1):62.
An, Sang Wook et al., Comparison of Hepatic Detoxification activity and reducing Serum Alcohol concentration of Hovenia dulsis $T_{HUNB}$ and Alnus japonica Steud, Korean J. Medicinal Crop Sci. 7(4): 263-268 (1999) https://ww.semanticscholar.org/paper/Comparison-of-Hepatic-Detoxification-aetivity-and-An-Kim/a32fb2cc818c6b8bea61009dd9aff6507950076.
Berk M, Dean OM, Cotton SM, Jeavons S, Tanious M, Kohlmann K, Hewitt K, Moss K, Allwang C, Schapkaitz I et al., "The efficacy of adjunctive N-acetylcysteine in major depressive disorder: a double-blind, randomized, placebo-controlled trial," J Clin Psychiatry 2014, 75(6):628-636.
Cederbaum Al, "Introduction-serial review: alcohol, oxidative stress and cell injury," Free Radic Biol Med 2001, 31(12):1524-1526.
Cederbaum Al, Wu D, Mari M, Bai J, "CYP2E1-dependent toxicity and oxidative stress in HepG2 cells," Free Radic Biol Med 2001, 31(12):1539-1543.
Chen SH, Zhong GS, Li AL, Li SH, Wu LK, "Influence of Hovenia dulcis on alcohol concentration in blood and activity of alcohol dehydrogenase (ADH) of animals after drinking," Zhongguo Zhong Yao Za Zhi 2006, 31(13):1094-1096 and English Abstract, 3 pages.
Clemente Plaza N, Reig Garcia-Galbis M, Martinez-Espinosa RM, "Effects of the Usage of I-Cysteine (I-Cys) on Human Health," Molecules 2018, 23(3).
Cobb CA, Cole MP, "Oxidative and nitrative stress in neurodegeneration," Neurobiol Dis 2015, 84:4-21.
Dean O, Giorlando F, Berk M, "N-acetylcysteine in psychiatry: current therapeutic evidence and potential mechanisms of action," J Psychiatry Neurosci 2011, 36(2):78-86.
Deepmala, Slattery J, Kumar N, Delhey L, Berk M, Dean O, Spielholz C, Frye R, "Clinical trials of N-acetylcysteine in psychiatry and neurology: A systematic review," Neurosci Biobehav Rev 2015, 55:294-321.
Eriksson CJP, Metsala M, Moykkynen T, Makisalo H, Karkkainen O, Palmen M, Salminen JE, Kauhanen J, "L-Cysteine Containing Vitamin Supplement Which Prevents or Alleviates Alcohol-related Hangover Symptoms: Nausea, Headache, Stress and Anxiety," Alcohol 2020, 55(6):660-666.
Fang HL, Lin HY, Chan MC, Lin WL, Lin WC, "Treatment of chronic liver injuries in mice by oral administration of ethanolic extract of the fruit of Hovenia dulcis," Am J Chin Med 2007, 35(4):693-703.
Goldberg DM, Watts C: Serum enzyme changes as evidence of liver reaction to oral alcohol. Gastroenterology 1965, 49(3):256-261.
Gunn C, Mackus M, Griffin C, Munafo MR, Adams S: A systematic review of the next-day effects of heavy alcohol consumption on cognitive performance. Addiction 2018, 113(12):2182-2193.
Isse T, Matsuno K, Oyama T, Kitagawa K, Kawamoto T, "Aldehyde dehydrogenase 2 gene targeting mouse lacking enzyme activity shows high acetaldehyde level in blood, brain, and liver after ethanol gavages," Alcohol Clin Exp Res 2005, 29(11):1959-1964.
Karadayian AG, Malanga G, Czerniczyniec A, Lombardi P, Bustamante J, Lores-Arnaiz S, "Free radical production and antioxidant status in brain cortex non-synaptic mitochondria and synaptosomes at alcohol hangover onset," Free Radic Biol Med 2017, 108:692-703.
Kim CJ, Kovacs-Nolan J, Yang C, Archbold T, Fan MZ, Mine Y, "L-cysteine supplementation attenuates local inflammation and restores gut homeostasis in a porcine model of colitis," Biochim Biophys Acta 2009, 1790(10):1161-1169.
Kim H, Kim YJ, Jeong HY, Kim JY, Choi EK, Chae SW, Kwon O, "A standardized extract of the fruit of Hovenia dulcis alleviated alcohol-induced hangover in healthy subjects with heterozygous ALDH2: A randomized, controlled, crossover trial," J Ethnopharmacol 2017, 209:167-174.
Kimura R, Murata T, "Effect of theanine on norepinephrine and serotonin levels in rat brain," Chem Pharm Bull (Tokyo) 1986, 34(7):3053-3057.
Kimura R, Murata T, "Influence of alkylamides of glutamic acid and related compounds on the central nervous system. I. Central depressant effect of theanine," Chem Pharm Bull (Tokyo) 1971, 19(6):1257-1261.
Lee HS, Isse T, Kawamoto T, Woo HS, Kim AK, Park JY, Yang M, "Effects and action mechanisms of Korean pear (Pyrus pyrifolia cv. Shingo) on alcohol detoxification," Phytother Res 2012, 26(11):1753-1758.
Lieber CS, "S-Adenosyl-L-methionine and alcoholic liver disease in animal models: implications for early intervention in human beings," Alcohol 2002, 27(3):173-177.
Loguercio C, Federico A, "Oxidative stress in viral and alcoholic hepatitis," Free Radic Biol Med 2003, 34(1):1-10.
Louvet A, Mathurin P, "Alcoholic liver disease: mechanisms of injury and targeted treatment," Nat Rev Gastroenterol Hepatol 2015, 12(4):231-242.
Marra F, Efsen E, Romanelli RG, Caligiuri A, Pastacaldi S, Batignani G, Bonacchi A, Caporale R, Laffi G, Pinzani M et al: Ligands of peroxisome proliferator-activated receptor gamma modulate profibrogenic and proinflammatory actions in hepatic stellate cells. Gastroenterology 2000, 119(2):466-478.
Minarini A, Ferrari S, Galletti M, Giambalvo N, Perrone D, Rioli G, Galeazzi GM, "N-acetylcysteine in the treatment of psychiatric disorders: current status and future prospects," Expert Opin Drug Metab Toxicol 2017, 13(3):279-292.
Mocelin R, Marcon M, D'Ambros S, Herrmann AP, da Rosa Araujo AS, Piato A, "Behavioral and Biochemical Effects of N-Acetylcysteine in Zebrafish Acutely Exposed to Ethanol," Neurochem Res 2018, 43(2):458-464.
Mocelin R, Herrmann AP, Marcon M, Rambo CL, Rohden A, Bevilaqua F, de Abreu MS, Zanatta L, Elisabetsky E, Barcellos LJ et al., "N-acetylcysteine prevents stress-induced anxiety behavior in zebrafish," Pharmacol Biochem Behav 2015, 139 Pt B:121-126.
Morais-Silva G, Alves GC, Marin MT, "N-acetylcysteine treatment blocks the development of ethanol-induced behavioural sensitization and related DeltaFosB alterations," Neuropharmacology 2016, 110(Pt A):135-142.
Ortiz GG, Pacheco Moises FP, Mireles-Ramirez M, Flores-Alvarado LJ, Gonzalez-Usigli H, Sanchez-Gonzalez VJ, Sanchez-Lopez AL, Sanchez-Romero L, Diaz-Barba El, Santoscoy-Gutierrez JF et al., "Oxidative Stress: Love and Hate History in Central Nervous System," Adv Protein Chem Struct Biol 2017, 108:1-31.
Ouyang Z, Xu G, Jiang Y, "I-Cysteine augments microtubule-associated protein 2 levels and enhances antioxidant activity in rats following traumatic brain injury," 3 Biotech 2019, 9(7):280.
Ozburn AR, Harris RA, Blednov YA, "Chronic voluntary alcohol consumption results in tolerance to sedative/hypnotic and hypothermic effects of alcohol in hybrid mice," Pharmacol Biochem Behav 2013, 104:33-39.
Ozkol H, Bulut G, Balahoroglu R, Tuluce Y, Ozkol HU, "Protective Effects of Selenium, N-Acetylcysteine and Vitamin E Against Acute Ethanol Intoxication in Rats,". Biol Trace Elem Res 2017, 175(1):177-185.
Padayatty SJ, Katz A, Wang Y, Eck P, Kwon O, Lee JH, Chen S, Corpe C, Dutta A, Dutta SK et al., "Vitamin C as an antioxidant: evaluation of its role in disease prevention," J Am Coll Nutr 2003, 22(1):18-35.

(56) References Cited

OTHER PUBLICATIONS

Preiss J, Handler P: Biosynthesis of diphosphopyridine nucleotide. I. Identification of intermediates. J Biol Chem 1958, 233(2):488-492.

Preiss J, Handler P: Biosynthesis of diphosphopyridine nucleotide. II. Enzymatic aspects. J Biol Chem 1958, 233(2):493-500.

Remington's Pharmaceutical Sciences, Mack Publishing Company, Easton, Pa., 18th edition, 1990.

Sadzuka Y, Inoue C, Hirooka S, Sugiyama T, Umegaki K, Sonobe T, "Effects of theanine on alcohol metabolism and hepatic toxicity," *Biol Pharm Bull* 2005, 28(9):1702-1706.

Sadzuka Y, Sugiyama T, Miyagishima A, Nozawa Y, Hirota S: The effects of theanine, as a novel biochemical modulator, on the antitumor activity of adriamycin. *Cancer Lett* 1996, 105(2):203-209.

Santos P, Herrmann AP, Benvenutti R, Noetzold G, Giongo F, Gama CS, Piato AL, Elisabetsky E., "Anxiolytic properties of N-acetylcysteine in mice," *Behav Brain Res* 2017, 317:461-469.

Schneider R, Jr., Santos CF, Clarimundo V, Dalmaz C, Elisabetsky E, Gomez R, "N-acetylcysteine prevents behavioral and biochemical changes induced by alcohol cessation in rats," *Alcohol* 2015, 49(3):259-263.

Schneider R, Jr., Bandiera S, Souza DG, Bellaver B, Caletti G, Quincozes-Santos A, Elisabetsky E, Gomez R, "N-acetylcysteine Prevents Alcohol Related Neuroinflammation in Rats," *Neurochem Res* 2017, 42(8):2135-2141.

Shen Y, Lindemeyer AK, Gonzalez C, Shao XM, Spigelman I, Olsen RW, Liang J, "Dihydromyricetin as a novel anti-alcohol intoxication medication," *J Neurosci* 2012, 32(1):390-401.

Siegmund S, Haas S, Schneider A, Singer MV: Animal models in gastrointestinal alcohol research-a short appraisal of the different models and their results. *Best Pract Res Clin Gastroenterol* 2003, 17(4):519-542.

Sugiyama T, Sadzuka Y, "Theanine, a specific glutamate derivative in green tea, reduces the adverse reactions of doxorubicin by changing the glutathione level," *Cancer Lett* 2004, 212(2):177-184.

Swift R, Davidson D, "Alcohol hangover: mechanisms and mediators," *Alcohol Health Res World* 1998, 22(1):54-60.

Thorrisen MM, Bonsaksen T, Hashemi N, Kjeken I, van Mechelen W, Aas RW: Association between alcohol consumption and impaired work performance (presenteeism): a systematic review. BMJ Open 2019, 9(7):e029184.

Wiese J, McPherson S, Odden MC, Shlipak MG: Effect of Opuntia ficus indica on symptoms of the alcohol hangover. Arch Intern Med 2004, 164(12):1334-1340.

Xiang J, Zhu W, Li Z, Ling S, "Effect of juice and fermented vinegar from Hovenia dulcis peduncles on chronically alcohol-induced liver damage in mice," *Food Funct* 2012, 3(6):628-634.

Yoshikawa M, Murakami T, Ueda T, Yoshizumi S, Ninomiya K, Murakami N, Matsuda H, Saito M, Fujii W, Tanaka T et al., "Bioactive constituents of Chinese natural medicines. III. Absolute stereostructures of new dihydroflavonols, hovenitins I, II, and III, isolated from hoveniae semen seu fructus, the seed and fruit of *Hovenia dulcis* THUNB. (*Rhamnaceae*): inhibitory effect on alcohol-induced muscular relaxation and hepatoprotective activity," *Yakugaku Zasshi* 1997, 117(2):108-118.

International Search Report and Written Opinion for International Application No. PCT/US21/59570, dated Feb. 3, 2022, 9 pages.

* cited by examiner

ACTIVE INGREDIENT COMPLEXES, COMPOSITIONS AND METHODS FOR HANGOVER RELIEF AND TO AMELIORATE ALCOHOL-INDUCED LIVER DAMAGE

BACKGROUND

Alcohol is a psychoactive substance that has been consumed by several cultures for centuries. However, drinking in excess leads to drunkenness, which can cause hangover symptoms, including unpleasant physical, physiological and psychological experiences, such as nausea, headache, stress and anxiety. These sequelae may last from less than one hour to several days, depending on many internal and external factors, and can lead to impaired cognitive function and daily activity performance (such as driving), as well as impaired work performance and absenteeism.

In addition, excessive alcohol consumption can lead to alcoholism, which in turn, can lead to many diseases, such as Alcoholic Liver Disease (ALD). Long-term drinking and subsequent damage to the liver cause various changes in cells and molecules which may damage liver metabolism. According to the US Centers for Disease Control and Prevention, approximately 88,000 people die from alcohol-related health problems every year, making alcohol-related health problems the third most preventable cause of death in the United States. Additionally, according to the World Health Organization, worldwide, alcohol consumption causes 3 million deaths every year, accounting for 5.1% of the global disease burden. There is currently no effective medicine to treat these diseases and the symptoms related to alcohol consumption without serious side effects.

SUMMARY

According to embodiments of the present disclosure, an active ingredient complex includes NADH (nicotinamide adenine dinucleotide (NAD)+hydrogen (H)) or a pharmaceutically acceptable salt or derivative thereof, L-cysteine or a pharmaceutically acceptable salt or derivative thereof, Dihydromyricetin (DHM) or a pharmaceutically acceptable salt or derivative thereof, N-acetyl-cysteine (NAC) or a pharmaceutically acceptable salt or derivative thereof, L-theanine or a pharmaceutically acceptable salt or derivative thereof, and buffered vitamin C or a pharmaceutically acceptable salt or derivative thereof.

In some embodiments, the NADH, DHM, NAC, L-Cysteine, L-theanine and Buffered Vitamin C may be present in the active ingredient complex at a weight ratio of 1 (NADH): 15-20 (L-Cysteine): 25-35 (DHM):5-10 (NAC):1-5 (L-theanine):1-5 (Buffered Vitamin C).

According to some embodiments, the NADH may be present in the active ingredient complex relative to one or more of the DHM, NAC, L-cysteine, L-theanine and Buffered Vitamin C at any one or more of the following weight ratios:

1 NADH:15-20 L-Cysteine; and/or
1 NADH:25-35 DHM; and/or
1 NADH:5-10 NAC; and/or
1 NADH:1-5 L-theanine; and/or
1 NADH:1-5 Buffered Vitamin C.

In some embodiments, the NADH may be present in the active ingredient complex in an amount of about 0.5 to 2.5 wt % based on a total combined weight of the NADH, L-Cysteine, DHM, NAC, L-theanine and Buffered Vitamin C. According to some embodiments, the L-Cysteine may be present in the active ingredient complex in an amount of about 20 to 40 wt % based on a total combined weight of the NADH, L-Cysteine, DHM, NAC, L-theanine and Buffered Vitamin C. In some embodiments, the DHM may be present in the active ingredient complex in an amount of about 40 to 60 wt % based on a total combined weight of the NADH, L-Cysteine, DHM, NAC, L-theanine and Buffered Vitamin C. According to some embodiments, the NAC is present in the active ingredient complex in an amount of about 5 to 20 wt % based on a total combined weight of the NADH, L-Cysteine, DHM, NAC, L-theanine and Buffered Vitamin C. In some embodiments, the L-theanine may be present in the active ingredient complex in an amount of about 1 to 10 wt % based on a total combined weight of the NADH, L-Cysteine, DHM, NAC, L-theanine and Buffered Vitamin C. According to some embodiments, the Buffered Vitamin C is present in the active ingredient complex in an amount of about 1 to 10 wt % based on a total combined weight of the NADH, L-Cysteine, DHM, NAC, L-theanine and Buffered Vitamin C.

In some embodiments, a pharmaceutical composition includes the active ingredient complex according to embodiments of the present disclosure, and one or more pharmaceutically acceptable carriers, excipients, adjuvants and/or diluents. According to some embodiments, the pharmaceutical composition may include a tablet, capsule or powder.

In some embodiments, a dietary supplement composition includes the active ingredient complex according to embodiments of the present disclosure, and one or more pharmaceutically acceptable carriers, excipients, adjuvants and/or diluents. According to some embodiments, the dietary supplement composition may include a tablet, capsule or powder.

According to some embodiments, a method of treating, reducing the likelihood of developing, reducing the severity of, or ameliorating acute alcoholic liver damage in a subject includes administering to the subject an active ingredient complex according to embodiments of the present disclosure. In some embodiments, administration of the active ingredient complex may include administering the active ingredient complex prior to the subject consuming or being exposed to alcohol. According to some embodiments, the administration of the active ingredient may include orally administering to the subject a dietary supplement including the active ingredient composition. In some embodiments, the administration of the active ingredient complex may include administering a dose of the active ingredient complex of about 0.01 mg/kg to about 50 mg/kg per day.

In some embodiments, a method of increasing a subject's tolerance of alcohol includes administering to the subject an active ingredient complex according to embodiments of the present disclosure. According to some embodiments, the administration of the active ingredient complex may include administering the active ingredient complex prior to the subject consuming or being exposed to alcohol. In some embodiments, the administration of the active ingredient may include orally administering to the subject a dietary supplement including the active ingredient composition. According to some embodiments, the administration of the active ingredient complex may include administering a dose of the active ingredient complex of about 0.01 mg/kg to about 50 mg/kg per day.

According to some embodiments, a method of treating, reducing the likelihood of developing, reducing the severity of, or alleviating the symptoms of an alcohol hangover in a subject includes administering to the subject an active ingredient complex according to embodiments of the present disclosure. In some embodiments, the administration of the active ingredient complex includes administering the active ingredient complex prior to the subject consuming or being exposed to alcohol. According to some embodiments, the administration of the active ingredient includes orally administering to the subject a dietary supplement including the active ingredient composition. In some embodiments, the administration of the active ingredient complex includes administering a dose of the active ingredient complex of about 0.01 mg/kg to about 50 mg/kg per day.

BRIEF DESCRIPTION OF THE DRAWINGS

These and other features and advantages of embodiments of the present disclosure may be better understood by reference to the following detailed description when considered in conjunction with the accompanying drawings, in which.

DETAILED DESCRIPTION

Figure 1A:
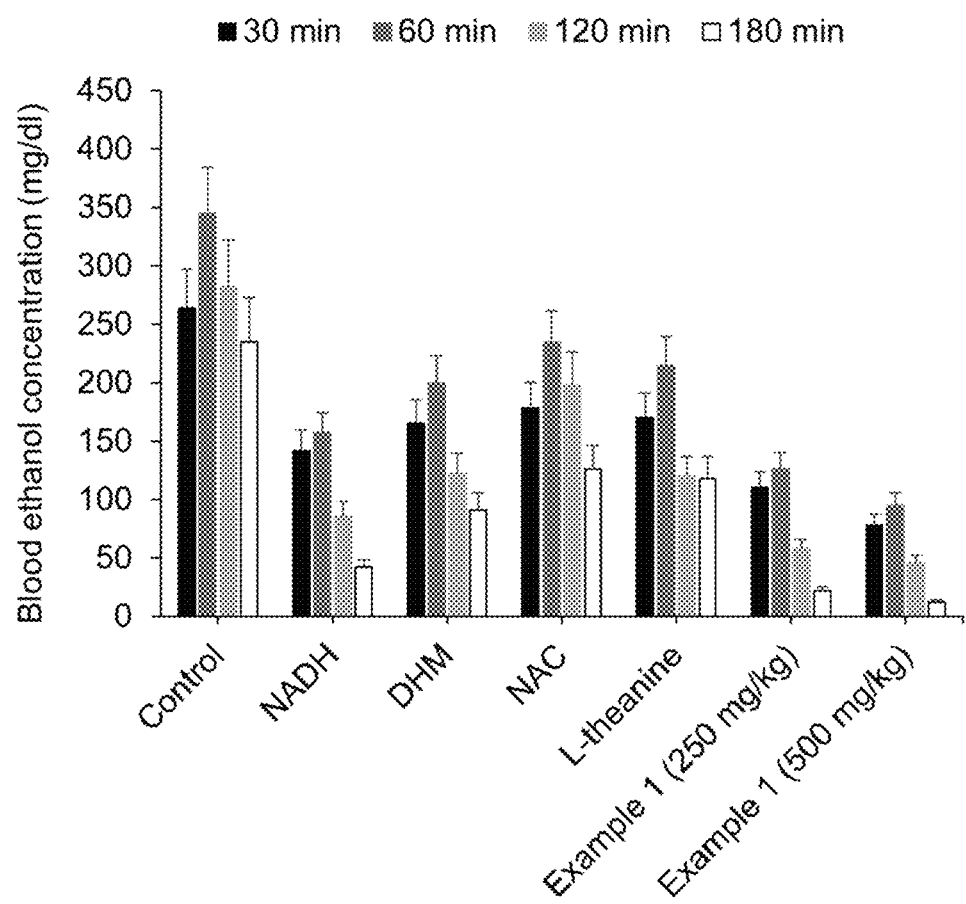
FIG. 1A is a graph comparing the blood alcohol (ethanol) concentration vs. time (after ethanol administration) of mice administered with 500 mg/kg NADH, 500 mg/kg DHM, 500 mg/kg (N-acetyl-cysteine) (NAC), 500 mg/kg L-theanine, 250 mg/kg Example 1, 500 mg/kg Example 1, or vehicle 15 min prior to 8 ml/kg ethanol ingestion (40% w/v, in tap water)

According to embodiments of the present disclosure, a pharmaceutical or neutraceutical (e.g., dietary supplement) composition includes generally harmless, efficient substances and is effective for relieving, alleviating or ameliorating hangover symptoms, or for preventing or reducing the likelihood of developing hangover symptoms or liver function damage, or for treating liver function damage. In some embodiments, for example, the composition accelerates alcohol metabolism, alleviates acute alcohol-induced hepatotoxicity, and inhibits or alleviates symptoms of discomfort (e.g., hangover symptoms) caused by alcohol consumption (or overconsumption). In some embodiments, for example, the composition may include an active ingredient complex that is NADH efficient and anti-alcoholic, and that relieves, alleviates or ameliorates hangover symptoms, or prevents or reduces the likelihood of developing hangover symptoms or liver function damage, or for treating liver function damage. According to some embodiments, the active ingredient composition can be incorporated into the pharmaceutical or neutraceutical composition in any suitable manner, for example, into a tablet, powder or capsule for oral administration, etc., as is discussed further below.

In some embodiments, the active ingredient complex may include (i.e., comprise, consist essentially of, or consist of NADH (i.e., nicotinamide adenine dinucleotide (NAD)+ hydrogen (H)), dihydromyricetin (DHM), N-acetyl-cysteine (NAC), L-Cysteine, L-theanine and Buffered Vitamin C, or pharmaceutically acceptable salts or derivatives thereof. According to some embodiments, the active ingredient complex may contain the NADH, dihydromyricetin (DHM), N-acetyl-cysteine (NAC), L-Cysteine, L-theanine and Buffered Vitamin C (or pharmaceutically acceptable salts or derivatives thereof) at a weight ratio of 1 (NADH):15-20 (L-Cysteine): 25-35 (DHM):5-10 (NAC):1-5 (L-theanine): 1-5 (Buffered Vitamin C). For example, in some embodiments, the active ingredient complex may contain the NADH, dihydromyricetin (DHM), N-acetyl-cysteine (NAC), L-Cysteine, L-theanine and Buffered Vitamin C (or pharmaceutically acceptable salts or derivatives thereof) at a weight ratio of 1 (NADH):17-19 (L-Cysteine): 28-32 (DHM):6-9 (NAC):1-3 (L-theanine):1-3 (Buffered Vitamin C). And in some embodiments, the active ingredient complex may contain the NADH, dihydromyricetin (DHM), N-acetyl-cysteine (NAC), L-Cysteine, L-theanine and Buffered Vitamin C (or pharmaceutically acceptable salts or derivatives thereof) at a weight ratio of 1 (NADH):18 (L-Cysteine): 30 (DHM):7.2 (NAC):2 (L-theanine):2 (Buffered Vitamin C).

In some embodiments, for example, the active ingredient complex may contain the NADH (or pharmaceutically acceptable salt(s) or derivative(s) thereof) relative to one or more of the dihydromyricetin (DHM), N-acetyl-cysteine (NAC), L-Cysteine, L-theanine and Buffered Vitamin C (or pharmaceutically acceptable salts or derivatives thereof) at any one or more of the following weight ratios:

1) 1 NADH:15-20 L-Cysteine, or 1 NADH:17-19 L-Cysteine, or 1 NADH to 18 L-Cysteine; and/or
2) 1 NADH:25-35 DHM, or 1 NADH:28-32 DHM, or 1 NADH:30 DHM; and/or
3) 1 NADH:5-10 NAC, or 1 NADH:6-9 NAC, or 1 NADH:7.2 NAC; and/or
4) 1 NADH:1-5 L-theanine, or 1 NADH:1-3 L-theanine, or 1 NADH:2 L-theanine; and/or
5) 1 NADH:1-5 Buffered Vitamin C, or 1 NADH:1-3 Buffered Vitamin C, or 1 NADH:2 Buffered Vitamin C.

In some embodiments, the NADH (or pharmaceutically acceptable salt(s) or derivative(s) thereof) may be present in the active ingredient complex in an amount of about 0.5 to 2.5 wt %, based on the total weight of the active ingredient complex (i.e., the total, combined weight of the NADH, L-Cysteine, DHM, NAC, L-theanine and Buffered Vitamin C). For example, in some embodiments, the NADH may be present in the active ingredient complex in an amount of about 1 to 2 wt %, or about 1.5 to 2 wt %, or about 1.6 to 1.7 wt % or 1.66 wt %, based on the total weight of the active ingredient complex.

According to some embodiments, the L-Cysteine (or pharmaceutically acceptable salt(s) or derivative(s) thereof) may be present in the active ingredient complex in an amount of about 20 to 40 wt %, based on the total weight of the active ingredient complex (i.e., the total, combined weight of the NADH, L-Cysteine, DHM, NAC, L-theanine and Buffered Vitamin C). For example, in some embodiments, the L-Cysteine may be present in the active ingredient complex in an amount of about 25 to 35 wt %, or about 28 to 32 wt %, or about 30 wt % or 29.9 wt %, based on the total weight of the active ingredient complex.

In some embodiments, the DHM (or pharmaceutically acceptable salt(s) or derivative(s) thereof) may be present in the active ingredient complex in an amount of about 40 to 60 wt %, based on the total weight of the active ingredient complex (i.e., the total, combined weight of the NADH, L-Cysteine, DHM, NAC, L-theanine and Buffered Vitamin C). For example, in some embodiments, the DHM may be present in the active ingredient complex in an amount of about 45 to 55 wt %, or about 48 to 52 wt %, or about 50 wt % or 49.8 wt %, based on the total weight of the active ingredient complex.

According to some embodiments, the NAC (or pharmaceutically acceptable salt(s) or derivative(s) thereof) may be present in the active ingredient complex in an amount of about 5 to 20 wt %, based on the total weight of the active ingredient complex (i.e., the total, combined weight of the NADH, L-Cysteine, DHM, NAC, L-theanine and Buffered Vitamin C). For example, in some embodiments, the NAC may be present in the active ingredient complex in an amount of about 8 to 15 wt %, or about 10 to 14 wt %, or about 12 wt % or 11.9 wt %, based on the total weight of the active ingredient complex.

In some embodiments, the L-theanine (or pharmaceutically acceptable salt(s) or derivative(s) thereof) may be present in the active ingredient complex in an amount of about 1 to 10 wt %, based on the total weight of the active ingredient complex (i.e., the total, combined weight of the NADH, L-Cysteine, DHM, NAC, L-theanine and Buffered Vitamin C). For example, in some embodiments, the L-theanine may be present in the active ingredient complex in an amount of about 1 to 8 wt %, or about 1 to 5 wt %, or about 3 wt % or 3.3 wt %, based on the total weight of the active ingredient complex.

According to some embodiments, the Buffered Vitamin C (or pharmaceutically acceptable salt(s) or derivative(s) thereof) may be present in the active ingredient complex in an amount of about 1 to 10 wt %, based on the total weight of the active ingredient complex (i.e., the total, combined weight of the NADH, L-Cysteine, DHM, NAC, L-theanine and Buffered Vitamin C). For example, in some embodiments, the Buffered Vitamin C may be present in the active ingredient complex in an amount of about 1 to 8 wt %, or about 1 to 5 wt %, or about 3 wt % or 3.3 wt %, based on the total weight of the active ingredient complex.

In some embodiments, for example, the active ingredient complex may include about 1.66 wt % NADH, about 29.90 wt % L-cysteine, about 49.83 wt % DHM, about 11.96 wt % NAC, about 3.32 wt % L-theanine, and about 3.32 wt % Buffered Vitamin C.

As discussed above, the active ingredient complex includes NADH, L-cysteine, DHM, NAC, L-theanine and Buffered Vitamin C (or pharmaceutically acceptable salts or derivatives thereof). These ingredients work together synergistically to provide the unexpected benefits of relieving, alleviating or ameliorating hangover symptoms, preventing or reducing the likelihood of developing hangover symptoms or liver function damage, and/or treating liver function damage. Indeed, while the individual ingredients of the active ingredient complex have unique functions, mixing them in the proportions disclosed herein enable them to achieve their maximum efficacy by coordinating and promoting each other in a synergistic manner.

Example Unique Properties of NADH

As discussed in U.S. application Ser. No. 17/221,734 (filed on Apr. 2, 2021, titled "METHODS OF AMELIORATING THE EFFECTS OF ALCOHOLIC LIVER DAMAGE," and having a common Applicant and Assignee with the present disclosure), NADH has anti-alcoholism effects and ameliorative effects on acute alcoholic liver injury. The mechanisms of NADH in achieving these effects are also discussed in U.S. application Ser. No. 17/221,734, the entire content of which is incorporated herein by reference, and attached to this disclosure as an Appendix (and therefore constitutes a part of this disclosure). NADH is a coenzyme existing in all living cells, and as shown in the NADH structure depicted below, contains two nucleotides connected by 5'-phosphate groups, one of which contains an adenine base and the other contains nicotinamide.

Structure of NADH

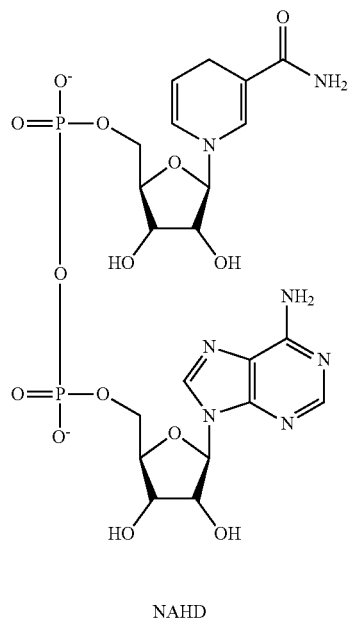

NAHD

As discussed in U.S. application Ser. No. 17/221,734, NADH is an effective NAD+ concentration-enhancing agent. And as compared to nicotinamide mononucelotide (NMN), for example, NADH can provide greater NAD+ increases at the same concentrations. U.S. application Ser. No. 17/221,734 also shows that intraperitoneal injection of NADH in C57BL/6J mice also significantly increased the NAD+ content in liver, blood, brain and fat. Importantly, NADH significantly increased the liver NAD+/NADH ratio, but did not induce apoptosis markers in cells. NADH-treated cells are resistant to cell death caused by NAD+-depleting genotoxins, e.g. hydrogen peroxide. Therefore, administration of NADH to mice can modify the liver redox fraction, NAD+/NADH, in a physiological manner, allowing the dehydrogenase reaction to work further towards the ethanol oxidation direction.

NAD+ is a necessary compound for cell respiration and a key coenzyme existing in all living cells. NAD+ plays the role of electron carrier in oxidation and reduction biochemical reactions in metabolism. The role of $NAD^+$ in cell respiration is well known. When glucose and fatty acids are oxidized, $NAD^+$ can accept a hydride equivalent, which leads to its reduction to NADH. NADH may provide a hydride equivalent, resulting in oxidation back to NAD+. These reduction-oxidation cycles use NAD+ to temporarily store hydride ions, but they do not consume NAD+.

Another major function of NAD+ is to participate in alcohol metabolism. Enzymes related to alcohol metabolism, such as alcohol dehydrogenase (ADH) and aldehyde dehydrogenase (ALDH), utilize NAD+ to drive the chain reaction of alcohol oxidation metabolism. Therefore, NAD+ plays an important role in the metabolism and detoxification of alcohol, as shown in Reaction Scheme 1 below.

Reaction Scheme 1: Alcohol oxidative metabolism

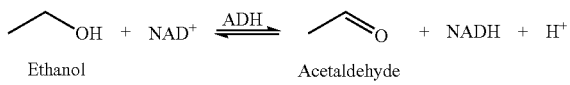

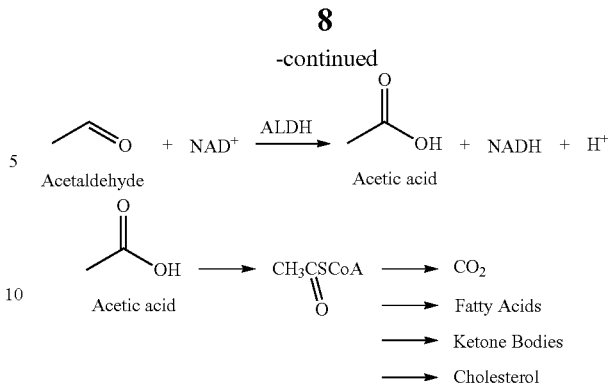

As shown in Reaction Scheme 1, the first step of alcohol metabolism is catalyzed by ADH, which mainly exists in the liver and includes a series of isomers. NAD+ needs to accept the reducing equivalents (hydrogen atoms and electrons) from the alcohol. As a result, ethanol is oxidized to acetaldehyde and vitamin cofactor, and $NAD_+$ is reduced to NADH and H+. The ADH reaction is reversible.

The second step is catalyzed by ALDH. Acetaldehyde is oxidized to acetate, and NAD+ is a cofactor which is reduced to NADH. This ALDH reaction is basically irreversible. Most of the acetaldehyde produced by alcohol oxidation is oxidized into acetate in the liver. Under normal circumstances, the circulating level of acetaldehyde is very low.

In the third step, most of the acetate produced by acetaldehyde oxidation leaves the liver and circulates to the surrounding tissue, where it is activated as a key Acetyl CoA. The carbon atoms from alcohol are ultimately the same as the products produced by the oxidation of carbohydrates, fats and proteins, including carbon dioxide, fatty acids, ketone bodies and cholesterol, and which products are formed depends on energy status and nutritional and hormonal conditions.

This indicates that NADH has the potential to promote alcohol metabolism and prevent (or reduce the likelihood of developing) early liver injury, or ameliorating the effects of early liver injury caused by acute alcohol exposure. Therefore, NADH is used as an active ingredient in the active ingredient complex to prevent (or reduce the likelihood of developing) hangover symptoms (or other harmful effects of drinking or excessive drinking), and/or to relieve or alleviate hangover symptoms (or other harmful effects of drinking or excessive drinking). NADH can also be used as an effective pharmacological agent to enhance NAD+ concentrations in cells and tissues, for example in preventing (or reducing the likelihood of developing) liver function damage, and/or recovering liver function damage caused by alcohol and other detrimental factors.

Example Unique Properties of Dihydromyricetin

Dihydromyricetin (DHM) is an extract from Japanese grape seed trees and has been used as an anti-hangover herb and hangover treatment in traditional medicine in Korea and China. For example, DHM has been used to treat headache and hangover, and recent studies have shown that DHM can reduce blood alcohol level and protect the liver from alcohol-induced damage.

Studies and anecdotal reports also show that when users take DHM after drinking alcohol, they experience fewer headaches, and less nausea, vomiting and anxiety. Scientists at the University of California, Los Angeles and the USC School of Pharmacy recently conducted a study in which DHM was administered to drunken mice. The results show that DHM has anti-oxidation, anti-inflammatory, anti-cancer and liver protection effects in addition to anti-hangover benefits. See Shen Y, Lindemeyer A K, Gonzalez C, Shao X M, Spigelman I, Olsen R W, Liang J, "Dihydromyricetin as a novel anti-alcohol intoxication medication," *J Neurosci* 2012, 32(1):390-401, the entire contents of which are incorporated herein by reference.

DHM is effective in the treatment of many alcohol-related symptoms because it has an effect on acetaldehyde. Most of the negative reactions to alcohol intake come from the accumulation of acetaldehyde in the body, which is a toxic by-product of alcohol. However, under the influence of DHM, the process of decomposing acetaldehyde is accelerated. A study has revealed that DHM can reduce blood alcohol levels in mice, suggesting that DHM can help metabolize alcohol faster and more effectively, which can relieve drunkenness and hangover symptoms. See https://www.semanticscholar.org/paper/Comparison-of-Hepatic-Detoxification-activity-and-An-Kim/a32fb2cc818cf6b8bea61009dd9aff6507950076 the entire content of which is incorporated herein by reference. Another study has demonstrated that DHM can prevent muscle relaxation induced by alcohol in rats. See Yoshikawa M, Murakami T, Ueda T, Yoshizumi S, Ninomiya K, Murakami N, Matsuda H, Saito M, Fujii W, Tanaka T et al., "Bioactive constituents of Chinese natural medicines. III. Absolute stereostructures of new dihydroflavonols, hovenitins I, II, and III, isolated from hoveniae semen seu fructus, the seed and fruit of Hovenia *dulcis* THUNB. (Rhamnaceae): inhibitory effect on alcohol-induced muscular relaxation and hepatoprotective activity," Yakugaku Zasshi 1997, 117(2):108-118, the entire content of which is incorporated herein by reference. Thus, without being bound by any particular theory, it is believed that DHM can be used to combat the lack of coordination usually associated with drunkenness or over-consumption of alcohol.

Two enzymes—alcohol dehydrogenase (ADH), and acetaldehyde dehydrogenase (ALDH)—facilitate the bodily break down alcohol. Studies have shown that DHM enhances the activity of these enzymes, suggesting that DHM can help the body metabolize alcohol faster. See Chen S H, Zhong G S, Li A L, Li S H, Wu L K, "Influence of Hovenia *dulcis* on alcohol concentration in blood and activity of alcohol dehydrogenase (ADH) of animals after drinking," Zhongguo Zhong Yao Za Zhi 2006, 31(13):1094-1096, the entire content of which is incorporated herein by reference. Theoretically, the sooner the blood alcohol level reaches zero, the sooner the hangover symptoms will disappear. A recent study showed that compared with those who did not take DHM, those who took DHM had fewer headaches, and less dizziness, nausea and weakness during a hangover. See Kim H, Kim Y J, Jeong H Y, Kim J Y, Choi E K, Chae S W, Kwon 0, "A standardized extract of the fruit of Hovenia *dulcis* alleviated alcohol-induced hangover in healthy subjects with heterozygous ALDH2: A randomized, controlled, crossover trial," *J Ethnopharmacol* 2017, 209: 167-174, the entire content of which is incorporated herein by reference.

Besides the antialcoholic effects of DHM, studies have demonstrated that DHM can also prevent (and help repair) alcohol-induced liver damage. See Xiang J, Zhu W, Li Z, Ling S, "Effect of juice and fermented vinegar from Hovenia *dulcis* peduncles on chronically alcohol-induced liver damage in mice," *Food Funct* 2012, 3(6):628-634; and Fang H L, Lin H Y, Chan M C, Lin W L, Lin W C, "Treatment of chronic liver injuries in mice by oral administration of ethanolic extract of the fruit of Hovenia *dulcis,*" *Am J Chin Med* 2007, 35(4):693-703, the entire contents of all of which are incorporated herein by reference. DHM has been used in the treatment of liver diseases in traditional Chinese medicine, and some studies show that DHM has the potential to treat alcohol withdrawal syndrome and also reduce the desire to drink. See Shen Y, Lindemeyer A K, Gonzalez C, Shao X M, Spigelman I, Olsen R W, Liang J, "Dihydromyricetin as a novel anti-alcohol intoxication medication," *J Neurosci* 2012, 32(1):390-401, the entire content of which is incorporated herein by reference. Accordingly, without being bound by any particular theory, it is believed that DHM can reduce withdrawal symptoms including anxiety, tolerance and epilepsy.

DHM can also have the beneficial effect of reducing the accumulation of lipid (fat) in liver tissue. Excessive alcohol will have a negative impact on liver metabolism, resulting in fat accumulation, augmented stress, and eventually develop into liver diseases for example liver cirrhosis.

Additionally, DHM can reduce inflammatory factors, also known as cytokines. Excessive alcohol can cause the liver to release cytokines, which can cause cell damage to the liver and other organs.

Without being bound by any particular theory or conclusion, it is believed that these findings support the effectiveness of DHM as a treatment to relieve, alleviate or ameliorate the symptoms of a hangover, and to prevent (or reduce) liver damage induced by ethanol by changing lipid metabolism, enhancing ethanol metabolism, and inhibiting inflammatory reaction, thereby promoting liver health. It is also believed that DHM may also help patients who have early warning signs of liver injury. As such, it is believed that DHM can be used to help restore and prolong liver function, and delay (or prevent or reduce the likelihood of) the occurrence of liver disease.

Example Unique Properties of N-Acetyl-Cysteine (NAC)

Alcohol consumption leads to the production of a highly toxic metabolite—acetaldehyde—which reacts with protein, phospholipids and nucleic acids, and actively participates in the production of reactive oxygen species (ROS). See Louvet A, Mathurin P, "Alcoholic liver disease: mechanisms of injury and targeted treatment," *Nat Rev Gastroenterol Hepatol* 2015, 12(4):231-242, the entire content of which is incorporated herein by reference. Excessive production of ROS—including superoxides, hydrogen peroxides and hydroxyl radicals—may exceed the antioxidant capacity of cells, resulting in oxidative damage. See Cobb C A, Cole M P, "Oxidative and nitrative stress in neurodegeneration," *Neurobiol Dis* 2015, 84:4-21; and Ortiz G G, Pacheco Moises F P, Mireles-Ramirez M, Flores-Alvarado L J, Gonzalez-Usigli H, Sanchez-Gonzalez V J, Sanchez-Lopez A L, Sanchez-Romero L, Diaz-Barba El, Santoscoy-Gutierrez J F et al., "Oxidative Stress: Love and Hate History in Central Nervous System," *Adv Protein Chem Struct Biol* 2017, 108:1-31, the entire contents of all of which are incorporated herein by reference. The increase in acetaldehyde concentration and imbalance of cell redox homeostasis can cause unpleasant symptoms of acute drinking, such as fatigue, headache, increased sensitivity to light and sound, dizziness, vertigo and emotional changes. See Karadayian A G, Malanga G, Czerniczyniec A, Lombardi P, Bustamante J, Lores-Arnaiz S, "Free radical production and antioxidant status in brain cortex non-synaptic mitochondria and synaptosomes at alcohol hangover onset," *Free Radic Biol Med* 2017, 108:692-703; and Swift R, Davidson D, "Alcohol hangover: mechanisms and mediators," *Alcohol Health Res World* 1998, 22(1):54-60, the entire contents of all of which are incorporated herein by reference.

N-acetylcysteine (NAC) is a precursor of glutathione (GSH) with strong antioxidant properties, anti-inflammatory (reducing pro-inflammatory cytokines) and neuro-nutrition activity, and can regulate various neurotransmitter systems, especially glutamate. See Deepmala, Slattery J, Kumar N, Delhey L, Berk M, Dean O, Spielholz C, Frye R, "Clinical trials of N-acetylcysteine in psychiatry and neurology: A systematic review," *Neurosci Biobehav Rev* 2015, 55:294-321; and Minarini A, Ferrari S, Galletti M, Giambalvo N, Perrone D, Rioli G, Galeazzi G M, "N-acetylcysteine in the treatment of psychiatric disorders: current status and future prospects," *Expert Opin Drug Metab Toxicol* 2017, 13(3): 279-292, the entire contents of all of which are incorporated herein by reference. Pre-clinical and clinical studies have revealed that NAC is a multi-target drug acting through neuroprotection, antioxidation and neurotrophic mechanisms. See Deepmala, Slattery J, Kumar N, Delhey L, Berk M, Dean O, Spielholz C, Frye R, "Clinical trials of N-acetylcysteine in psychiatry and neurology: A systematic review," *Neurosci Biobehav Rev* 2015, 55:294-321; Berk M, Dean O M, Cotton S M, Jeavons S, Tanious M, Kohlmann K, Hewitt K, Moss K, Allwang C, Schapkaitz I et al., "The efficacy of adjunctive N-acetylcysteine in major depressive disorder: a double-blind, randomized, placebo-controlled trial," *J Clin Psychiatry* 2014, 75(6):628-636; Dean O, Giorlando F, Berk M, "N-acetylcysteine in psychiatry: current therapeutic evidence and potential mechanisms of action," *J Psychiatry Neurosci* 2011, 36(2):78-86; Mocelin R, Herrmann A P, Marcon M, Rambo C L, Rohden A, Bevilaqua F, de Abreu M S, Zanatta L, Elisabetsky E, Barcellos L J et al., "N-acetylcysteine prevents stress-induced anxiety behavior in zebrafish," *Pharmacol Biochem Behav* 2015, 139 Pt B: 121-126; Santos P, Herrmann A P, Benvenutti R, Noetzold G, Giongo F, Gama C S, Piato A L, Elisabetsky E., "Anxiolytic properties of N-acetylcysteine in mice," *Behav Brain Res* 2017, 317:461-469; Schneider R, Jr., Santos C F, Clarimundo V, Dalmaz C, Elisabetsky E, Gomez R, "N-acetylcysteine prevents behavioral and biochemical changes induced by alcohol cessation in rats," *Alcohol* 2015, 49(3):259-263; and Schneider R, Jr., Bandiera S, Souza D G, Bellaver B, Caletti G, Quincozes-Santos A, Elisabetsky E, Gomez R, "N-acetylcysteine Prevents Alcohol Related Neuroinflammation in Rats," *Neurochem Res* 2017, 42(8):2135-2141, the entire contents of all of which are incorporated herein by reference. Specifically, with regard to the effect on alcoholism, studies have shown that NAC has beneficial effects on behavior (e.g., preventing the decrease of exploratory behavior), proinflammatory cytokines (e.g., preventing the increase of interleukin-18, IL-1b, IL-6 and TNF-α) and oxidative stress (e.g., decreasing the total oxidation state). See Schneider R, Jr., Santos C F, Clarimundo V, Dalmaz C, Elisabetsky E, Gomez R, "N-acetylcysteine prevents behavioral and biochemical changes induced by alcohol cessation in rats," *Alcohol* 2015, 49(3): 259-263; Schneider R, Jr., Bandiera S, Souza D G, Bellaver B, Caletti G, Quincozes-Santos A, Elisabetsky E, Gomez R, "N-acetylcysteine Prevents Alcohol Related Neuroinflammation in Rats," *Neurochem Res* 2017, 42(8):2135-2141; Morais-Silva G, Alves G C, Marin M T, "N-acetylcysteine treatment blocks the development of ethanol-induced behavioural sensitization and related DeltaFosB alterations," *Neuropharmacology* 2016, 110 (Pt A):135-142; Ozkol H, Bulut G, Balahoroglu R, Tuluce Y, Ozkol H U, "Protective Effects of Selenium, N-Acetylcysteine and Vitamin E Against Acute Ethanol Intoxication in Rats,". *Biol Trace Elem Res* 2017, 175(1):177-185; and Mocelin R, Marcon M, D'Ambros S, Herrmann A P, da Rosa Araujo A S, Piato A, "Behavioral and Biochemical Effects of N-Acetylcysteine in Zebrafish Acutely Exposed to Ethanol," *Neurochem Res* 2018, 43(2): 458-464, the entire contents of all of which are incorporated herein by reference.

Example Unique Properties of L-Cysteine

L-cysteine is a semi-essential amino acid for normal growth and function of the human body. The human body naturally contains a very small amount of L-cysteine, so food and supplements must be used to meet this demand. L-cysteine combines with other amino acids—such as glutamine and glycine—to form a potent antioxidant, namely glutathione. L-cysteine exists in various foods rich in protein, such as meat, dairy products, eggs, beans, nuts and seeds.

Recently, the effect of L-cysteine on the symptoms of an alcohol hangover were studied. See Eriksson C J P, Metsala M, Moykkynen T, Makisalo H, Karkkainen O, Palmen M, Salminen J E, Kauhanen J, "L-Cysteine Containing Vitamin Supplement Which Prevents or Alleviates Alcohol-related Hangover Symptoms: Nausea, Headache, Stress and Anxiety," *Alcohol* 2020, 55(6):660-666, the entire content of which is incorporated herein by reference. Using a randomized, double-blind, placebo-controlled method, the effects of two doses of L-cysteine (600 mg and 1200 mg) on the severity of alcoholic hangover symptoms were studied. Correlation analysis shows that L-cysteine has a positive effect on preventing or alleviating hangover symptoms. After a dose of 1200 mg, it was reported that the self-assessed severity of the hangover, nausea and headache improved, while the dose of 600 mg relieved stress and anxiety. The researchers of this study believe that L-cysteine can not only prevent or treat hangover symptoms, but also diminish the risk of alcohol addiction.

L-cysteine has many other health benefits as well. For example, L-cysteine can be used as an auxiliary substance for diabetes treatment, because it helps to lower blood sugar, decrease insulin resistance in the body, and prevent blood vessel damage. See Achari A E, Jain S K, "l-Cysteine supplementation increases insulin sensitivity mediated by upregulation of GSH and adiponectin in high glucose treated 3T3-L1 adipocytes," *Arch Biochem Biophys* 2017, 630:54-65; and Clemente Plaza N, Reig Garcia-Galbis M, Martinez-Espinosa R M, "Effects of the Usage of l-Cysteine (l-Cys) on Human Health," *Molecules* 2018, 23(3), the entire contents of all of which are incorporated herein by reference.

L-cysteine can also help treat colitis, which is an inflammatory intestinal disease. See Kim C J, Kovacs-Nolan J, Yang C, Archbold T, Fan M Z, Mine Y, "L-cysteine supplementation attenuates local inflammation and restores gut homeostasis in a porcine model of colitis," *Biochem Biophys Acta* 2009, 1790(10):1161-1169, the entire content of which is incorporated herein by reference.

Additionally, taking an L-cysteine supplement for one week can help enhance antioxidant activity in the body, thus decreasing the excessive production of free radicals caused by exercise. See Ouyang Z, Xu G, Jiang Y, "l-Cysteine augments microtubule-associated protein 2 levels and enhances antioxidant activity in rats following traumatic brain injury," 3 *Biotech* 2019, 9(7):280, the entire content of which is incorporated herein by reference.

Example Unique Properties of L-Theanine

L-theanine is an amino acid, which mainly exists in tea leaves and in small amounts in Bay Bolete mushrooms. L-theanine is synthesized from glutamic acid (glutamate) and ethylamine in the root of the tea tree, and then transported to the leaves. L-theanine is not naturally produced by human body, and it is not one of the essential amino acids.

However, L-theanine has various uses and health benefits. Theanine, a glutamic acid derivative, is widely used as a supplement (e.g., in drinks) since it has brain and nerve function. For example, theanine can have a relaxing effect attributable to the induction of alpha waves. See Kimura R, Murata T, "Effect of theanine on norepinephrine and serotonin levels in rat brain," *Chem Pharm Bull* (Tokyo) 1986, 34(7):3053-3057; and Kimura R, Murata T, "Influence of alkylam ides of glutamic acid and related compounds on the central nervous system. I. Central depressant effect of theanine," *Chem Pharm Bull* (Tokyo) 1971, 19(6): 1257-1261, the entire contents of all of which are incorporated herein by reference.

Theanine has also been found helpful in the treatment of alcohol withdrawal symptoms. Acute drinking (just as illegal or controlled drugs and other harmful substances) can hinder glutamate receptor activity. When this happens, memory and motor coordination (e.g., the ability to walk/move correctly) often suffer. In addition, hindered glutamate receptor activity can be toxic to brain cells, which will lead to nerve degeneration. Interestingly, though, long-term drinking can lead to an increase in glutamate receptor expression. Thus, when abstaining from alcohol, the lack of alcohol will inhibit the high expression of glutamate receptors, resulting in a state of overexcitation. This can lead to seizures and other symptoms of alcohol withdrawal.

L-theanine is similar to glutamic acid in structure, mainly because this amino acid is synthesized from glutamic acid. Therefore, without being bound by any particular theory, it is believed that L-theanine supplementation can balance the impaired glutamatergic function of patients with alcohol addiction. After oral administration of L-theanine, the body can absorb and decompose the L-theanine like glutamine. In the kidney, this amino acid is broken down into glutamic acid and ethylamine. There is evidence that theanine crosses the blood-brain barrier within 30 minutes after oral administration. In addition, L-theanine can bind to glutamate receptors, although the binding affinity is not as great as that of L-glutamic acid. Although the binding affinity between L-theanine and glutamate receptors is weak, the interaction between L-theanine and glutamate receptors has a protective effect on the brain.

It has been suggested that excessive drinking can lead to the production of free radicals, reductions in GSH levels, and increases in liver lipid peroxide (LPO), which may, in turn, result in alcoholic liver injury. See Loguercio C, Federico A, "Oxidative stress in viral and alcoholic hepatitis," *Free Radic Biol Med* 2003, 34(1):1-10; Cederbaum A I, "Introduction-serial review: alcohol, oxidative stress and cell injury," *Free Radic Biol Med* 2001, 31(12):1524-1526; Cederbaum A I, Wu D, Mari M, Bai J, "CYP2E1-dependent toxicity and oxidative stress in HepG2 cells," *Free Radic Biol Med* 2001, 31(12):1539-1543; and Lieber C S, "S-Adenosyl-L-methionine and alcoholic liver disease in animal models: implications for early intervention in human beings," *Alcohol* 2002, 27(3):173-177, the entire contents of all of which are incorporated herein by reference. In the liver, theanine is metabolized and converted into glutamic acid, leading to an increase in GSH levels. See Sugiyama T, Sadzuka Y, "Theanine, a specific glutamate derivative in green tea, reduces the adverse reactions of doxorubicin by changing the glutathione level," *Cancer Lett* 2004, 212(2): 177-184, the entire content of which is incorporated herein by reference. Although theanine itself does not have antioxidant features, [42], without being bound by any particular theory or mechanism, it is believed that theanine intake will have an impact on oxidative stress and diseases due to its effect on increasing effective GSH levels. Accordingly, theanine may have a positive effect on alcoholic liver damage.

The effects of theanine on ethanol metabolism and hepatotoxicity have been studied by single administration of ethanol to mice. To assess the effect of theanine on ethanol metabolism and its toxicity, intraperitoneal injection of theanine and oral administration of ethanol were used, and it was observed that theanine has a protective effect with respect to alcoholic liver injury. See Sadzuka Y, Inoue C, Hirooka S, Sugiyama T, Umegaki K, Sonobe T, "Effects of theanine on alcohol metabolism and hepatic toxicity," *Biol Pharm Bull* 2005, 28(9):1702-1706, the entire content of which is incorporated herein by reference.

In addition to these benefits of L-theanine with respect to alcoholics and other addicts, L-theanine provided a number of additional benefits. For example, L-theanine can improve sleep. Specifically, L-theanine may be beneficial to men and women who have difficulty getting enough sleep at night. These effects may be due to the ability of L-theanine to reduce resting heart rate and promote relaxation. Lack of sleep can enhance levels of the stress hormone, cortisol, and stress may interfere with efforts to recover from alcohol addiction, and amplify the symptoms experienced by patients. As such, improvements in sleep can be especially beneficial for those who consume (or over-consume) alcohol.

L-theanine can also be useful in the management of blood pressure. In particular, L-theanine may be beneficial to people suffering from high blood pressure due to stress. L-theanine can also lower blood pressure by effectively controlling stress. As high blood pressure can be a symptom of abstinence from alcohol, L-theanine can be particularly beneficial for those patients who consume (or over-consume) alcohol.

In addition, L-theanine can strengthen the immune system. Specifically, L-theanine can improve human immune system function, and reduce the incidence of upper respiratory tract infections. L-theanine can also reduce inflammation and enhance immune defense. Because alcohol can inhibit many aspects of the immune system, the immune enhancement effect of L-theanine can be particularly helpful for those who consume (or over-consume) alcohol.

L-theanine can also improve attention span and attentiveness. And while L-theanine can provide this benefit when used on its own, enhancements in these improvements can be seen when L-theanine is used in other attention improvement ingredients, such as caffeine.

Additionally, L-theanine can lead to weight loss. For example, drinking L-theanine in tea can create umami flavor, which can help promote weight loss by, for example, curbing or suppressing appetite, promoting satiety and preventing overeating.

Example Unique Properties of Buffered Vitamin C

Buffered vitamin C combines highly absorbable vitamin C with buffer minerals such as (but not limited to) magnesium, potassium and calcium. The buffer minerals allow the use of higher doses of vitamin C without causing stomach discomfort (or minimizing stomach discomfort), and these minerals support proper muscle relaxation and contraction. Buffered vitamin C is an antioxidant, and can also increase glutathione levels, which can help the body avoid (or minimize) damage caused by acetaldehyde and the pro-inflammatory effect caused by alcohol. See Padayatty S J, Katz A, Wang Y, Eck P, Kwon O, Lee J H, Chen S, Corpe C, Dutta A, Dutta S K et al, "Vitamin C as an antioxidant: evaluation of its role in disease prevention," *J Am Coll Nutr*

2003, 22(1):18-35 The acidity of buffered vitamin C is lower than that of non-mineral bound ascorbic acid, which will help to replenish mineral reserves that are exhausted during drinking (or consumption or over-consumption of alcohol).

The active ingredient complexes according to embodiments of the present disclosure can accelerate alcohol metabolism, alleviate acute alcohol-induced hepatotoxicity, oxidative damage, and the abnormal lipid metabolism in acute alcoholic liver damage, as well as improve tolerance to acute alcohol exposure. Given the growing demand for effective non-drug treatments or preventatives for hangover and liver function damage, the active ingredient complexes according to embodiments of the present disclosure, which is free of (or minimizes) adverse or intolerable side effects, may have significant implications for metabolic health and ALD.

According to some embodiments, the active ingredient complex may be administered orally. Such oral administration is not particularly limited, and may be accomplished via a dietary supplement containing the active ingredient complex, or via a pharmaceutical composition following a regimen prescribed by a physician. The dietary supplement and/or pharmaceutical composition may be in solid or liquid form, and the solid form may include a tablet, capsule or powder (which powder may be administered in dry form, or may be dispersed or suspended in a liquid). In some embodiments, when the dietary supplement and/or pharmaceutical composition is in tablet form, the table may include a powder or pellet of the active ingredient complex together with an enteric coating. Enteric coatings are well known to those of ordinary skill in the art, and any suitable enteric coating may be used with the active ingredient complexes of the present disclosure.

In some embodiments, the dietary supplement and/or pharmaceutical composition may include the active ingredient complex in a therapeutically or prophylactically effective amount. In some embodiments, the dietary supplements and/or pharmaceutical compositions may include the active ingredient complex, as well as one or more pharmaceutically acceptable carriers, excipients, adjuvants or diluents. Acceptable carriers, excipients and diluents are well known in the art and can be selected with regard to the intended route of administration and standard practice. Some non-limiting examples include binders, lubricants, suspending agents, coating agents (e.g., enteric coatings), solubilizing agents, preserving agents, wetting agents, emulsifiers, surfactants, sweeteners, colorants, flavoring agents, odorants, buffers, antioxidants, stabilizing agents and/or salts.

In some embodiments, for example, the dietary supplements and/or pharmaceutical compositions may include at least one pharmaceutically acceptable carrier. The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, dietary supplements and/or pharmaceutical compositions according to embodiments of the present disclosure may contain, in addition to the active ingredient complex, one or more diluents, fillers, salts, buffers, stabilizers, solubilizers, and/or other materials well known in the art. The preparation of pharmaceutically acceptable formulations is described in, e.g., Remington's Pharmaceutical Sciences, Mack Publishing Company, Easton, Pa., 18th edition, 1990.

As used herein, the term "pharmaceutically acceptable salt" refers to salts that retain the desired biological activity of the active ingredient and exhibit minimal or no undesired toxicological effects. Non-limiting examples of suitable such pharmaceutically acceptable salts include acid addition salts formed with inorganic acids (for example, hydrochloric acid, hydrobromic acid, sulfuric acid, phosphoric acid, nitric acid, and the like), and salts formed with organic acids (such as, e.g., acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalene disulfonic acid, and polygalacturonic acid).

The active ingredients in the active ingredient complexes described herein may also be administered as pharmaceutically acceptable quaternary salts known to those skilled in the art, e.g., quaternary ammonium salts represented by —N(R)2-, wherein R is hydrogen, alkyl, or benzyl, and Z is a counterion (non-limiting examples of which include chloride, bromide, iodide, O-alkyl, toluenesulfonate, methylsulfonate, sulfonate, phosphate, or carboxylate (non-limiting examples of which include benzoate, succinate, acetate, glycolate, maleate, malate, citrate, tartrate, ascorbate, benzoate, cinnamoate, mandeloate, benzyloate, and diphenylacetate).

According to some embodiments, the active ingredient complex described herein may be present in the dietary supplement or pharmaceutical composition together with the pharmaceutically acceptable carrier or diluent in any suitable amount. For example, the active ingredient complex may be present in an amount sufficient to deliver a therapeutically or prophylactically effective amount of the active ingredient complex to a patient or subject without causing (or minimizing the risk of) serious toxic effects in the patient or subject. In some embodiments, for example, the active ingredient complex may be administered by any route in a dose of about 0.01 to 50 mg/kg per day or per dose, for example about 0.01 to 40 mg/kg per day or per dose, about 0.01 to 30 mg/kg per day or per dose, about 5 to about 30 mg/kg per day or per dose, or about 10 to about 30 mg/kg per day or per dose. In some embodiments, for example, the active ingredient complex may be administered in a dose of about 5 mg/kg per day (or per administration) to about 8 mg/kg per day (or per administration). As would be understood by those of ordinary skill in the art, the effective dosage range of pharmaceutically acceptable derivatives or salts of the various active ingredients in the active ingredient complex can be calculated based on the weight of the active ingredient complex, and the weight of the parent compound of the derivative or salt to be delivered. And if the derivative or salt exhibits activity in itself, the effective dosage can be estimated as above using the weight of the active ingredient complex, and the weight of the derivative, or by any other means known to those of ordinary skill in the art. As would be understood by those of ordinary skill in the art, the concentration, treatment or dietary supplement protocol, and administration route will vary depending on the particular patient and intended use (e.g., for hangover relief, or amelioration or treatment of liver injury), and on the extent of liver injury to be treated (or prevented, reduced or ameliorated).

Additionally, the dosage regimen for the administration of the active ingredient complex is not particularly limited, and may be determined on a case-by-case basis by the patient (or subject) or by a prescribing physician. However, it is understood that the dosage regimen may vary depending on the physiology of the subject (or patient), the desired outcome of the regimen (e.g., protection against possible future alcoholic liver damage, ameliorating the effects of current alcoholic liver damage, preventing or reducing the likelihood of developing a hangover, or relieving the symptoms of a hangover). In some embodiments, for example, a patient (or subject) administering the active ingredient complex as a dietary supplement (e.g., prior to consumption of alcohol to protect against possible future alcoholic liver damage, or to prevent or reduce the likelihood of developing a hangover, or to reduce the severity of the symptoms of a subsequent hangover) may take a daily dose of the active ingredient complex indefinitely. In some embodiments, for example, a patient (or subject) administering the active ingredient complex after consumption of alcohol (e.g., to ameliorate or treat the effects of current alcoholic liver damage, or the relieve the symptoms of a hangover) may take a daily dose of the active ingredient complex for a period time after alcohol consumption sufficient or effective to ameliorate or treat the effects of the alcoholic liver damage or the symptoms of the hangover. For example, in some embodiments, this patient (or subject) may take a daily dose for 1 day to 14 days, for 3 days to 14 days, or for 3 days to 10 days.

According to some embodiments, for example, an example tablet formulation including an active ingredient complex according to embodiments of the present disclosure may be as shown in Table 1 below. It is understood that this formulation is but one example of a suitable tablet formulation and a suitable active ingredient complex for use in, for example, a dietary supplement application, and that the present disclosure is not limited to the stated tablet or active ingredient complex formulation. Additionally, in some embodiments, the tablet formulation and active ingredient complex shown in Table 1 (and indeed any tablet and active ingredient formulation according to embodiments of the present disclosure) may be administered in a dosage regimen of two tablets per day. However, it is understood that the same daily dose of the active ingredient complex may be administered in a single tablet, or in any number of tablets, including more than two tablets. And it is also understood that the daily dose may be adjusted in any manner, including increasing or decreasing the amount of active ingredient complex in each tablet, or in each daily dose, such that, for example, a patient (or user) might take a single tablet amounting to half the daily dose listed in the below Examples, or might take three or more tablets amounting to more than the daily dose listed in the below Examples.

TABLE 1

Example Tablet Formulation (and daily dose protocol) including Active Ingredient Complex

| Ingredient | Dose (mg) - two tablets daily | Amount in 1 tablet (mg) | w/w % (solution) | wt % based on active ingredient complex |
|---|---|---|---|---|
| ACTIVE INGREDIENT COMPLEX | | | | |
| NADH | 25 | 12.5 | 0.503018 | 1.66 |
| L-Cysteine | 450 | 225 | 9.054326 | 29.90 |
| Dihydromyricetin (DHM) | 750 | 375 | 15.09054 | 49.83 |
| N-acetyl-cysteine (NAC) | 180 | 90 | 3.62173 | 11.96 |
| L-theanine | 50 | 25 | 1.006036 | 3.32 |
| Buffered Vitamin C | 50 | 25 | 1.006036 | 3.32 |
| ENTERIC COATING | | | | |
| Silica and Glyceryl Triacetate | 80 | 40 | 1.609658 | — |
| Tablet Total | 1585 | 792.5 | 31.89135 | — |

Experimental

The following examples and experiments are presented for illustrative purposes only, and do not limit the scope and content of the present disclosure.

In the following experiments, male C57BL/6J mice were orally fed with alcohol (52% w/v), the composition of Table 1 (as Example 1), or each individual active ingredient of the formulation of Table 1. The concentrations of ethanol and acetaldehyde in blood, as well as the loss of righting reflex (LORR) were evaluated to indicate alcohol metabolism. The plasma levels of aspartate aminotransferase (AST) and alanine transaminase (ALT) and the levels of malonaldehyde (MDA) and superoxide dismutase (SOD) in liver tissue were tested as an indication of alcohol-induced liver injury. As shown in the below experiments, treatment with the active ingredient complexes according to embodiments of the present disclosure can accelerate alcohol metabolism and prevent (reduce the likelihood of developing, or reduce the severity of) alcoholic liver injury caused by excessive drinking. Additionally, higher hepatic triglyceride (TG) contents and the activity of serum very low density lipoprotein (VLDL) in acute alcoholic-diet fed mice were also diminished by supplementing with Example 1, suggesting that the active ingredient complexes according to embodiments of the present disclosure can alleviate abnormal lipid metabolism in acute alcoholic liver damage.

As demonstrated, the active ingredient complexes according to embodiments of the present disclosure accelerate alcohol metabolism, alleviate acute alcohol-induced hepatotoxicity, and inhibit (or reduce the severity of) symptoms of discomfort caused by alcohol. Each ingredient in the formula contributes to the anti-hangover effects, and the mixture of these ingredients according to embodiments of the present disclosure creates a synergistic effect that yields a stronger anti-hangover effect that is higher than the effect achieved by any one single ingredient. Additionally, the mixture of these ingredients in the specific ratios disclosed herein also provides an additional synergy contributing to the improved anti-hangover and liver injury performance.

In the following examples and experiments, the below materials and methods were used, unless otherwise specified.

Animals

C57BL/6J male mice (The Jackson Laboratory; 40 days of age) were used. They were kept under standard laboratory conditions with a temperature of 22±1° C., dark/light cycles of 12/12 h, and relative humidity of 55±5%. All animals had free access to food and water, except that they fasted for 2 hours before administration.

Mice were randomly divided into a normal group (untreated group), a control group and a treatment group, with 8 mice in each group. The mice in treatment groups were intragastrically administered with 500 mg/kg NADH, 500 mg/kg DHM, 500 mg/kg (N-acetyl-cysteine) (NAC), 500 mg/kg L-theanine, 250 mg/kg of Example 1, 500 mg/kg of the Example 1, or a vehicle 15 min prior to one single dose of 8 ml/kg ethanol ingestion (52% w/v, in tap water). In the experiments, the vehicle used was phosphate-buffered saline (PBS), unless otherwise indicated This is the most commonly used animal alcohol intake to imitate human alcoholism, which is 5-6 g/kg body weight, equivalent to 0.75 L whisky (40% v/v) consumed by a 75 kg human body. The control group was given the same ethanol solution and corresponding distilled water, while the normal group was only given corresponding distilled water. At different time points of the experiment, the mice were anesthetized by intraperitoneal injection of 10% chloral hydrate (350 mg/kg body weight). Blood and liver tissues were extracted from each animal. Liver tissues were frozen immediately for the described bioanalyses.

Determination of Ethanol and Acetaldehyde Concentration in Blood

Eyeball blood samples (0.3 mL) were taken, each was put into an 8 mL headspace vial containing 1.2 mL 0.6 M perchloric acid, 0.5 mL trichloroacetic acid (10%) and 0.3 mL internal standard (160 mg/L tertiary butanol), and the concentrations of ethanol and acetaldehyde were determined with headspace gas chromatography. Ethanol and acetaldehyde were quantified by gas chromatography as described by Isse T, Matsuno K, Oyama T, Kitagawa K, Kawamoto T, "Aldehyde dehydrogenase 2 gene targeting mouse lacking enzyme activity shows high acetaldehyde level in blood, brain, and liver after ethanol gavages," *Alcohol Clin Exp Res* 2005, 29(11):1959-1964; and Lee H S, Isse T, Kawamoto T, Woo H S, Kim A K, Park J Y, Yang M, "Effects and action mechanisms of Korean pear (*Pyrus pyrifolia* cv. Shingo) on alcohol detoxification," *Phytother Res* 2012, 26(11):1753-1758, the entire contents of all of which are incorporated herein by reference.

Determination of Plasma Levels of AST and ALT

To evaluate the effects on alcoholic liver injury, male C57BL/6J mice were fasted for 12 h, and intragastrically administered with 500 mg/kg NADH, 500 mg/kg DHM, 500 mg/kg (N-acetyl-cysteine) (NAC), 500 mg/kg L-theanine, 250 mg/kg of the formulation of Table 1, 500 mg/kg of the formulation of Table 1, or vehicle 15 min prior to 8 ml/kg ethanol ingestion (40% w/v, in tap water). After treatment with alcohol for 6 hours, blood samples were taken to detect biochemical indices.

To evaluate therapeutic effects, all groups except the control group (which was given the same amount of normal saline) were given 40% ethanol every 24 h, which caused acute liver injury for 3 consecutive days. After three days of alcohol treatment, these mice were treated with 500 mg/kg NADH or 500 mg/kg of Example 1 every day for three consecutive days. Blood samples were collected in an anticoagulant test tube and centrifuged at 1500 rpm for 10 minutes to attain plasma. The plasma AST and ALT activity was determined with a commercial kit (Sigma-Aldrich) based on the manufacturer's instructions.

Determination of Liver SOD, MDA and TG Levels

Liver samples were prepared with homogenization in cold isotonic saline. The homogenate (10%, w/v) was centrifuged at 4500 g for 10 minutes and the supernatant was used for biochemical analysis. The MDA, SOD and TG levels were determined with commercial kits (Abcam, #ab118970; Thermofisher, #EIASODC and Abcam, ab65336), according to the manufacturer's instructions. The results were normalized to the total protein determined by BCA Protein Assay Kit (Abcam, #ab102536) according to the manufacturer's instructions.

VLDL Levels of Experimental Mice

The levels of VLDL in serum samples were examined with a Bio-Tek synergy2 Multiscan Spectrum (Botten Instruments Co.).

Determination of Loss of Righting Reflex

Alcohol acts on the central nervous system, causing various behavioral and/or cognitive problems, e.g., loss of righting reflex (LORR). The tolerance of mice to the hypnotic effect induced by alcohol can be assessed by the loss of righting reflex (LORR) test, as discussed in Ozburn A R, Harris R A, Blednov Y A, "Chronic voluntary alcohol consumption results in tolerance to sedative/hypnotic and hypothermic effects of alcohol in hybrid mice," *Pharmacol Biochem Behav* 2013, 104:33-39, the entire content of which is incorporated herein by reference. LORR is defined as the phenomenon that mice cannot correct themselves three times within 30 seconds after alcohol intake. LORR latency is defined as the time from drinking to occurrence of LORR, and LORR duration is defined as the time from occurrence to recovery of LORR.

Statistical Analysis

Differences between treatment groups and the control groups were analyzed by independent t test using the SPSS 20.0 statistical software. All results are expressed as means±SD. Differences of $p<0.05$ were considered statistically significant.

Effect on Blood Ethanol and Acetaldehyde Levels

Male C57BL/6J mice were fasted for 12 h, and intragastrically administered with 500 mg/kg NADH, 500 mg/kg DHM, 500 mg/kg (N-acetyl-cysteine) (NAC), 500 mg/kg L-theanine, 250 mg/kg Example 1, 500 mg/kg Example 1, or vehicle 15 min prior to 8 ml/kg ethanol ingestion (40% w/v, in tap water). Blood samples were collected from the infraorbital venous plexus at different time points (as indicated) after the ethanol administration. Blood ethanol (FIG. 1A) and acetaldehyde (FIG. 1B) levels were determined. Each group contained 6-8 mice. Data are presented as the mean±SD.

As shown in FIG. 1A, when NADH, DHM, NAC, L-theanine and Example 1 were administered orally 30 min before ethanol administration, they could significantly reduce ethanol in blood. As also shown, Example 1 had a stronger effect than any other single component, starting to play a role in 30 minutes. FIG. 1A also shows that the effect of Example 1 on reducing blood alcohol concentration can be dose-dependent, and the effect of 500 mg/kg is obviously better than that of 250 mg/kg (though the 250 mg/kg dose also shows good performance).

Figure 1B:
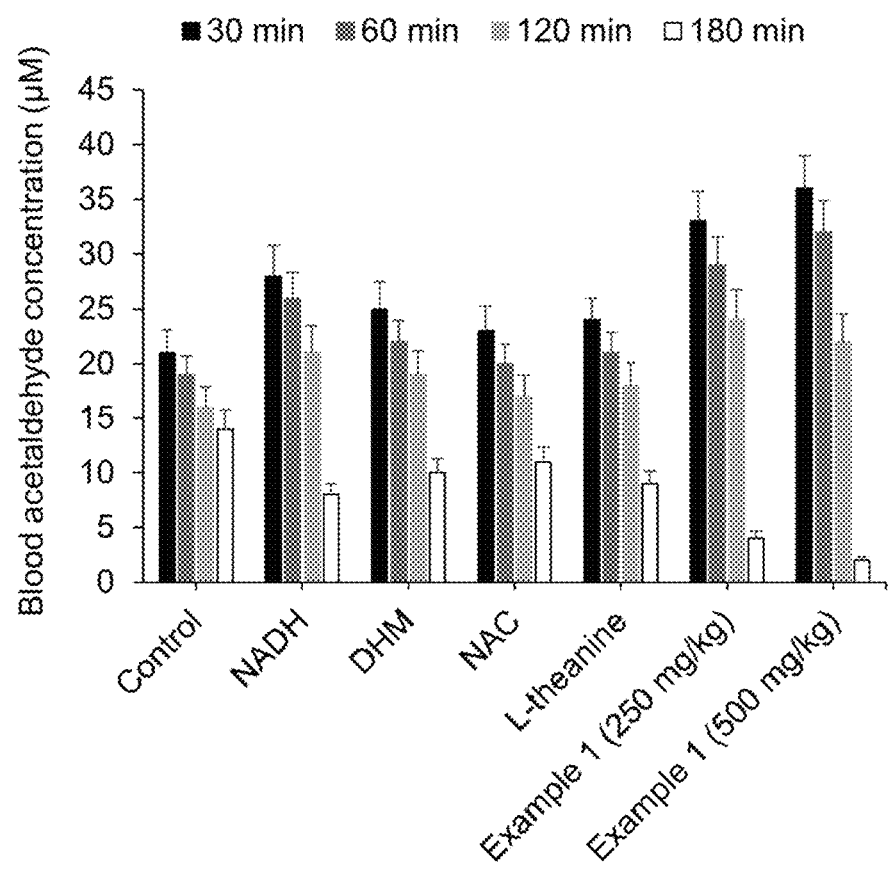
FIG. 1B is a graph comparing the blood acetaldehyde concentration vs. time (after ethanol administration) of mice administered with 500 mg/kg NADH, 500 mg/kg DHM, 500 mg/kg (N-acetyl-cysteine) (NAC), 500 mg/kg L-theanine, 250 mg/kg Example 1, 500 mg/kg Example 1, or vehicle 15 min prior to 8 ml/kg ethanol ingestion (40% w/v, in tap water)

Additionally, as shown in FIG. 1B, NADH and Example 1 treatments significantly increased blood acetaldehyde levels in mice between 30 minutes and two hours after ethanol administration, demonstrating these treatments could accelerate the first-pass speed of ethanol metabolism. Of note, after two hours, these treatments significantly reduced the acetaldehyde in the blood, and the effect of Example 1 was more significant than that of NADH and any other single component. These results all indicate that the active ingredient complexes according to embodiments of the present disclosure can accelerate alcohol metabolism and exhibit synergistic effects that are far superior to any other single component.

Alleviation of Acute Alcohol-Induced Hepatotoxicity

Liver marker enzymes in plasma, such as aspartate transaminase (AST) and alanine aminotransferase (ALT), are known as sensitive biochemical markers of early liver damage. Accordingly, the preventive and therapeutic effects of Example 1 and each individual active ingredient on acute alcoholic liver injury were assessed by determining the levels of AST and ALT in the plasma after ethanol consumption. Specifically, to evaluate the preventive and therapeutic effects on alcohol-induced hepatotoxicity, male C57BL/6J mice were fasted for 12 h, and intragastrically administered with 500 mg/kg NADH, 500 mg/kg DHM, 500 mg/kg (N-acetyl-cysteine) (NAC), 500 mg/kg L-theanine, 500 mg/kg of Example 1, or vehicle 30 min prior to 8 ml/kg ethanol ingestion (40% w/v, in tap water). After treatment with alcohol for 6 hours, blood samples were taken to detect biochemical indices. The plasma levels of AST (FIG. 2A) and ALT (FIG. 2B) were determined as described above.

Data are expressed as the mean±SD (n=8). *p<0.01 vs control; #p<0.01 vs alcohol exposure; $p<0.01 vs alcohol+NADH.

Figure 2A:
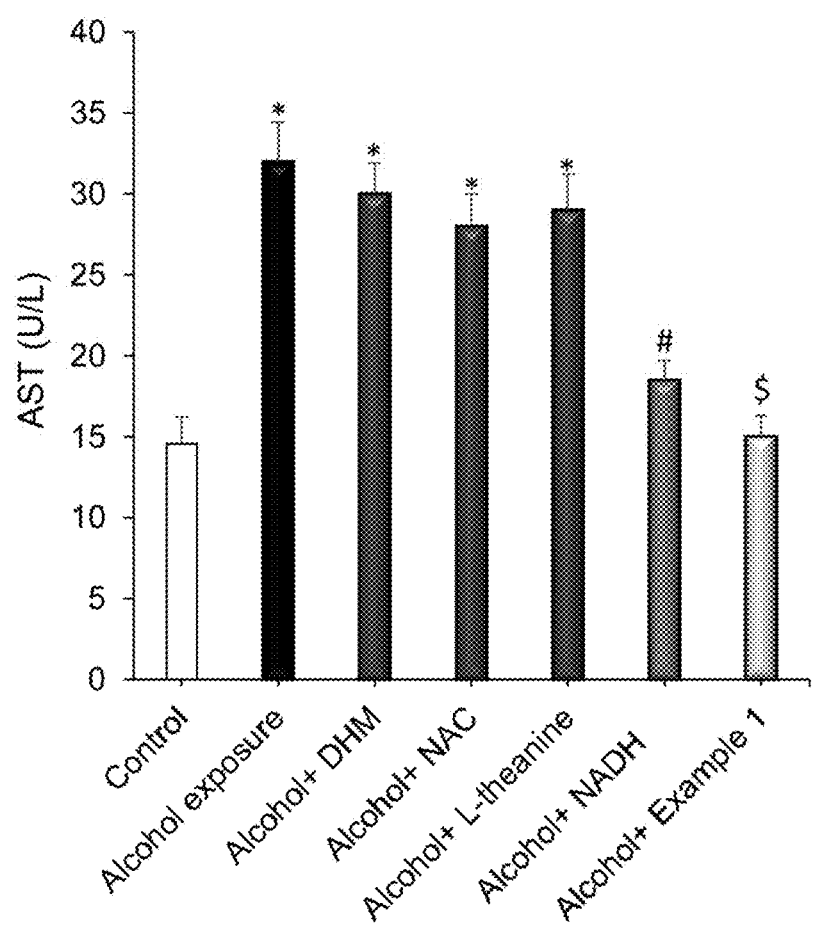
FIG. 2A is a graph comparing plasma levels of aspartate transaminase (AST) in male C57BL/6J mice intragastrically administered with 500 mg/kg NADH, 500 mg/kg DHM, 500 mg/kg (N-acetyl-cysteine) (NAC), 500 mg/kg L-theanine, 500 mg/kg Example 1, or vehicle 30 min prior to 8 ml/kg ethanol ingestion (40% w/v, in tap water)
Figure 2B:
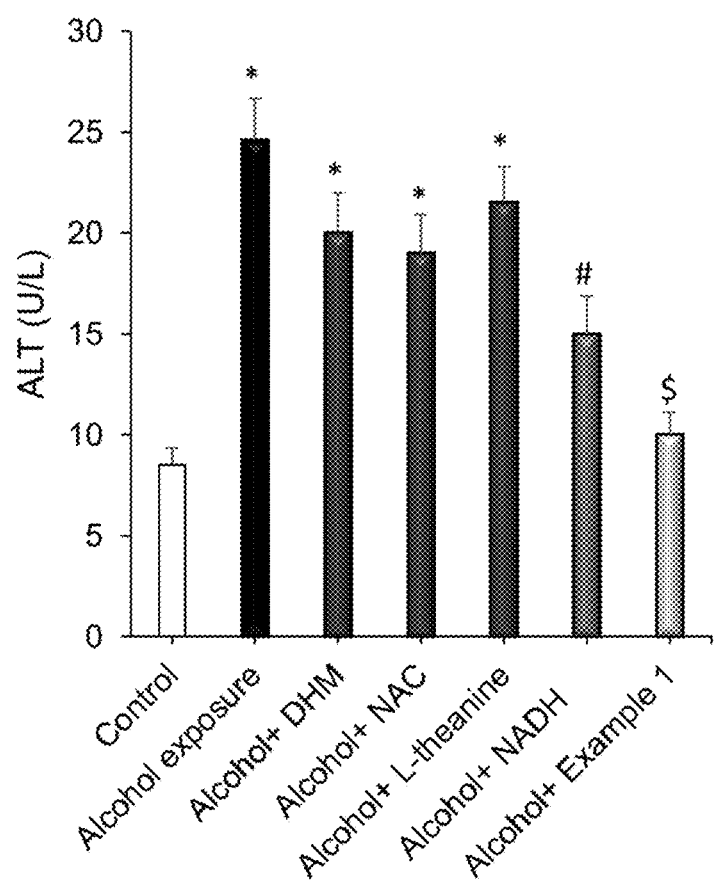
FIG. 2B is a graph comparing plasma levels of alanine aminotransferase (ALT) in male C57BL/6J mice intragastrically administered with 500 mg/kg NADH, 500 mg/kg DHM, 500 mg/kg (N-acetyl-cysteine) (NAC), 500 mg/kg L-theanine, 500 mg/kg Example 1, or vehicle 30 min prior to 8 ml/kg ethanol ingestion (40% w/v, in tap water)

As shown in FIGS. 2A and 2B, acute alcohol treatment dramatically increased plasma AST and ALT levels. Compared with the model group, intake of Example 1 and NADH in advance could significantly reduce plasma AST and ALT levels, indicating that Example 1 and NADH might protect liver tissue against acute alcohol toxicity. As can be seen, the effect of Example 1 is superior to any one single active ingredient.

Protective Effect Against Oxidative Damage Caused by Acute Alcohol Ingestion

Oxidative stress plays a pathogenic role in many liver diseases, such as hepatitis, non-alcoholic steatohepatitis (NASH), fibrosis, liver cirrhosis and liver cancer. Therefore, monitoring endogenous/exogenous antioxidants and enzymes implicated in free radical control can make imperative contributions to the occurrence and development of the diseases, and also can be considered as a good adjuvant for anti-oxidant therapy.

To compare the protective effect of Example 1 and each individual active ingredient on oxidative damage induced by acute alcohol intake in vivo, the biochemical indices, malondialdehyde (MDA) (an oxidative damage index) and superoxide dismutase (SOD) (an antioxidant indicator), in liver tissue were tested. Specifically, male C57BL/6J mice were fasted for 12 h, and intragastrically administered with 500 mg/kg NADH, 500 mg/kg DHM, 500 mg/kg (N-acetylcysteine) (NAC), 500 mg/kg L-theanine, 500 mg/kg Example 1, or vehicle 15 min prior to 8 ml/kg ethanol ingestion (40% w/v, in tap water). After treatment with alcohol for 6 hours, liver tissue was taken for determination of MDA (FIG. 3A) and SOD (FIG. 3B). Data are expressed as the mean±SD (n=8). *p<0.01 vs control; #p<0.01 vs alcohol exposure; $p<0.01 vs alcohol+NADH.

Figure 3A:
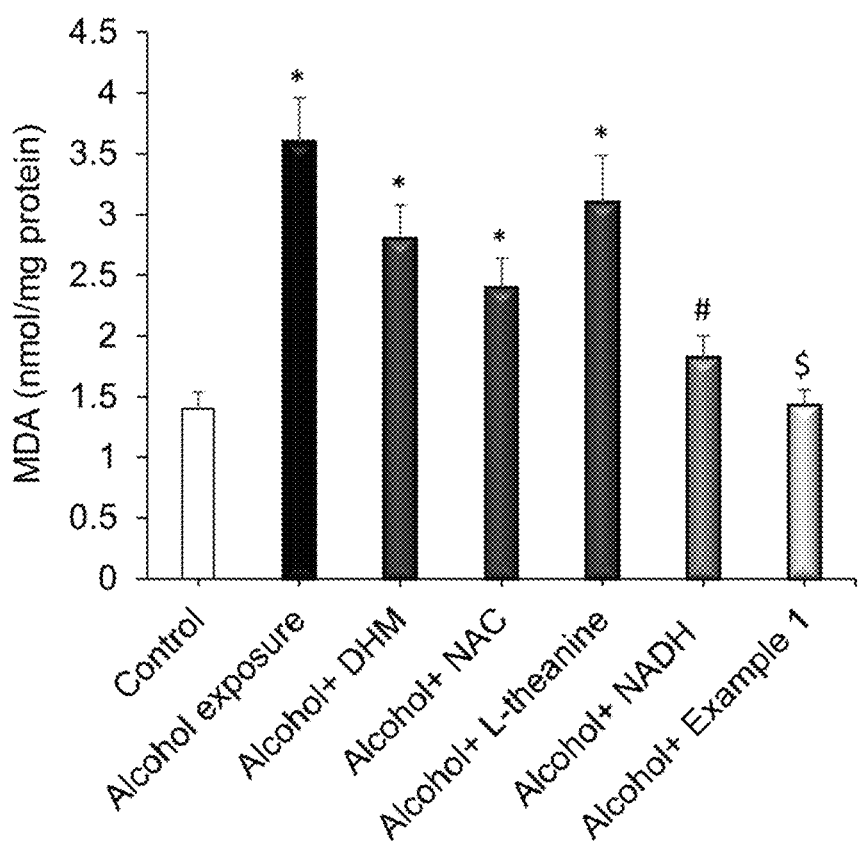
FIG. 3A is a graph comparing the malondiadehyde (MDA) activity of male C57BL/6J mice intragastrically administered with 500 mg/kg NADH, 500 mg/kg DHM, 500 mg/kg (N-acetyl-cysteine) (NAC), 500 mg/kg L-theanine, 500 mg/kg Example 1, or vehicle 15 min prior to 8 ml/kg ethanol ingestion (40% w/v, in tap water)
Figure 3B:
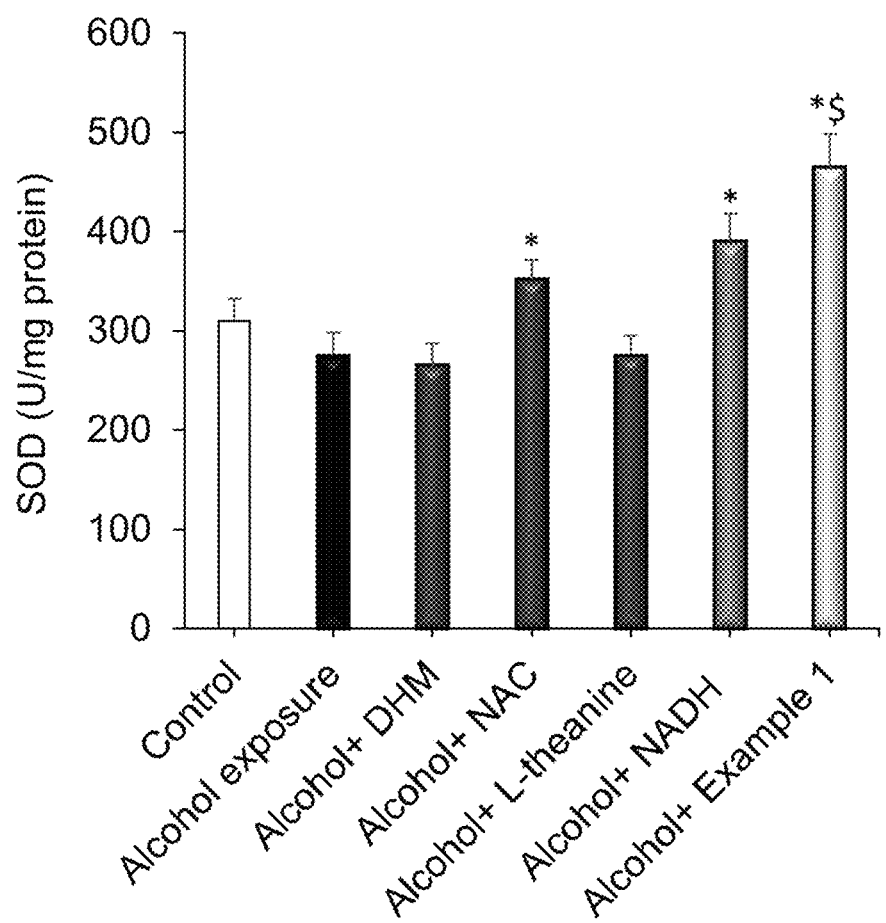
FIG. 3B is a graph comparing the superoxide dismutase (SOD) activity of male C57BL/6J mice intragastrically administered with 500 mg/kg NADH, 500 mg/kg DHM, 500 mg/kg (N-acetyl-cysteine) (NAC), 500 mg/kg L-theanine, 500 mg/kg Example 1, or vehicle 15 min prior to 8 ml/kg ethanol ingestion (40% w/v, in tap water)

As shown in FIGS. 3A and 3B, in the model group, SOD activity decreased, and the MDA level augmented dramatically, almost twice as much as that in the control group. As also shown in FIGS. 3A and 3B, administration of Example 1, NAC and NADH in advance can significantly reduce the MDA content in the liver, and increase SOD activity in alcohol-loaded mice. As can also be seen, the antagonistic effect of Example 1 on oxidative damage caused by acute alcohol intake is stronger than that of any one single active ingredient. Together, these results indicate that the active ingredient complexes according to embodiments of the present disclosure may effectively protect the liver from high oxidative stress caused by acute alcohol intake.

Effect on Lipid Metabolism

Figure 4A:
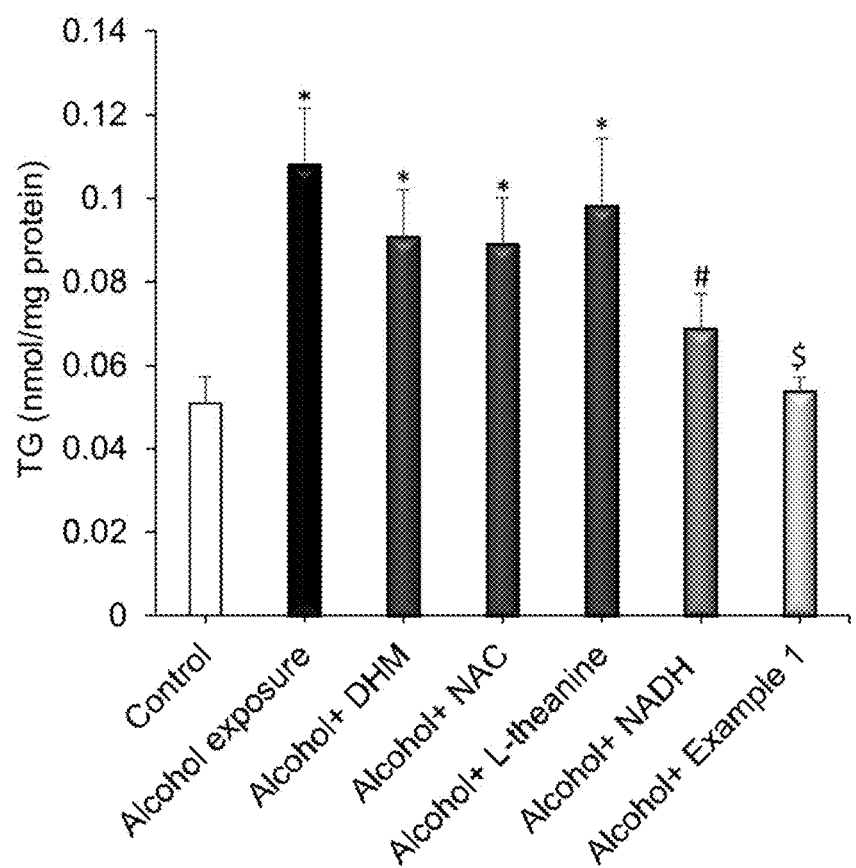
FIG. 4A is a graph comparing the triglyceride (TG) levels of male C57BL/6J mice after administration of 8 ml/kg ethanol (40% w/v, in tap water) alone, after pre-treatment with 500 mg/kg NADH, 500 mg/kg DHM, 500 mg/kg (N-acetyl-cysteine) (NAC), 500 mg/kg L-theanine, 500 mg/kg Example 1, or vehicle 15 min prior to administration of 8 ml/kg ethanol (40% w/v, in tap water)
Figure 4B:
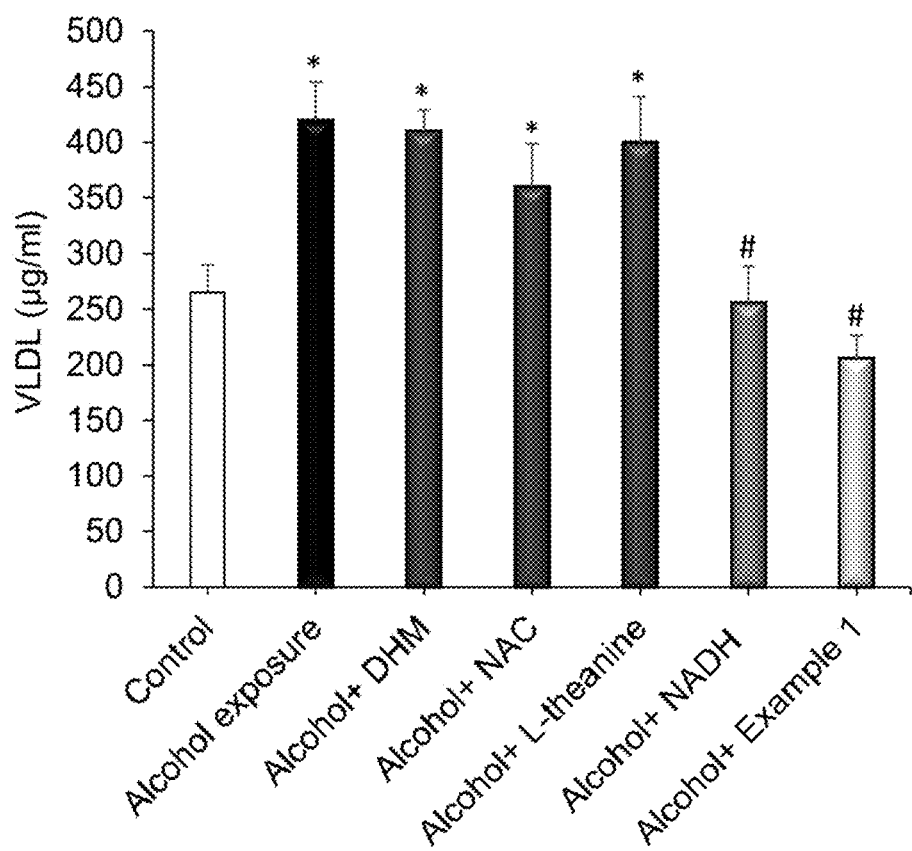
FIG. 4B is a graph comparing the activity of serum Very Low Density Lipoprotein (VLDL) of male C57BL/6J mice after administration of 8 ml/kg ethanol (40% w/v, in tap water) alone, after pre-treatment with 500 mg/kg NADH, 500 mg/kg DHM, 500 mg/kg (N-acetyl-cysteine) (NAC), 500 mg/kg L-theanine, 500 mg/kg Example 1, or vehicle 15 min prior to administration of 8 ml/kg ethanol (40% w/v, in tap water)

The index of liver lipid metabolism, the triglyceride (TG) level in liver tissue, and the activity of serum very low density lipoprotein (VLDL) were measured to evaluate alcoholic liver injury. Specifically, the mice treated as discussed above in connection with FIGS. 3A and 3B were used. The TG levels of the liver tissues from different groups are shown in FIG. 4A, and the serum VLDL levels (an index of liver lipid metabolism) are shown in FIG. 4B. Data are expressed as the mean±SD (n=8). *p<0.01 vs control; #p<0.01 vs alcohol exposure; $p<0.01 vs alcohol+NADH.

As shown in FIGS. 4A and 4B, compared with the normal control group, the liver TG and serum VLDL activities of mice exposed to alcohol alone increased by 2.2 times and 1.6 times respectively. And compared with the model control group (i.e., alcohol exposure alone), Example 1 and NADH pretreatment decreased the TG and VLDL levels in alcohol-loaded mice, while Example 1 had a stronger effect on reducing triglyceride than NADH. These results suggest that the active ingredient complexes according to embodiments of the present disclosure and NADH can alleviate abnormal lipid metabolism in acute alcoholic liver damage.

Effect on Tolerance to Acute Alcohol Exposure

Figure 5A:
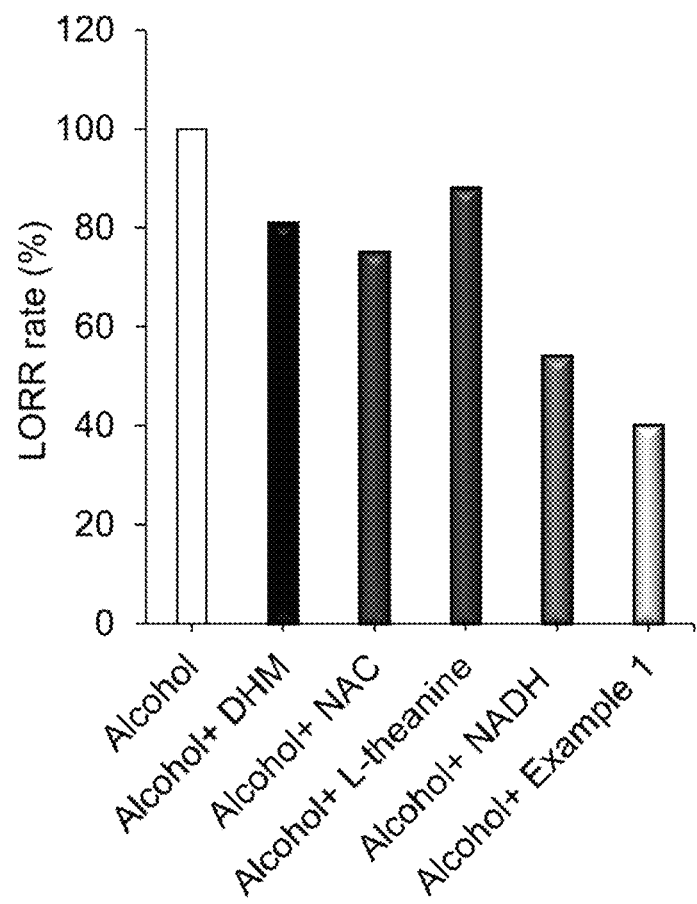
FIG. 5A is a graph comparing the LORR rate of male C57BL/6J mice after pre-treatment with 500 mg/kg NADH, 500 mg/kg DHM, 500 mg/kg (N-acetyl-cysteine) (NAC), 500 mg/kg L-theanine, 500 mg/kg Example 1 prior to administration of 8 ml/kg ethanol (40% w/v, in tap water) relative to male C57BL/6J mice after administration of 8 ml/kg ethanol (40% w/v, in tap water) alone.
Figure 5B:
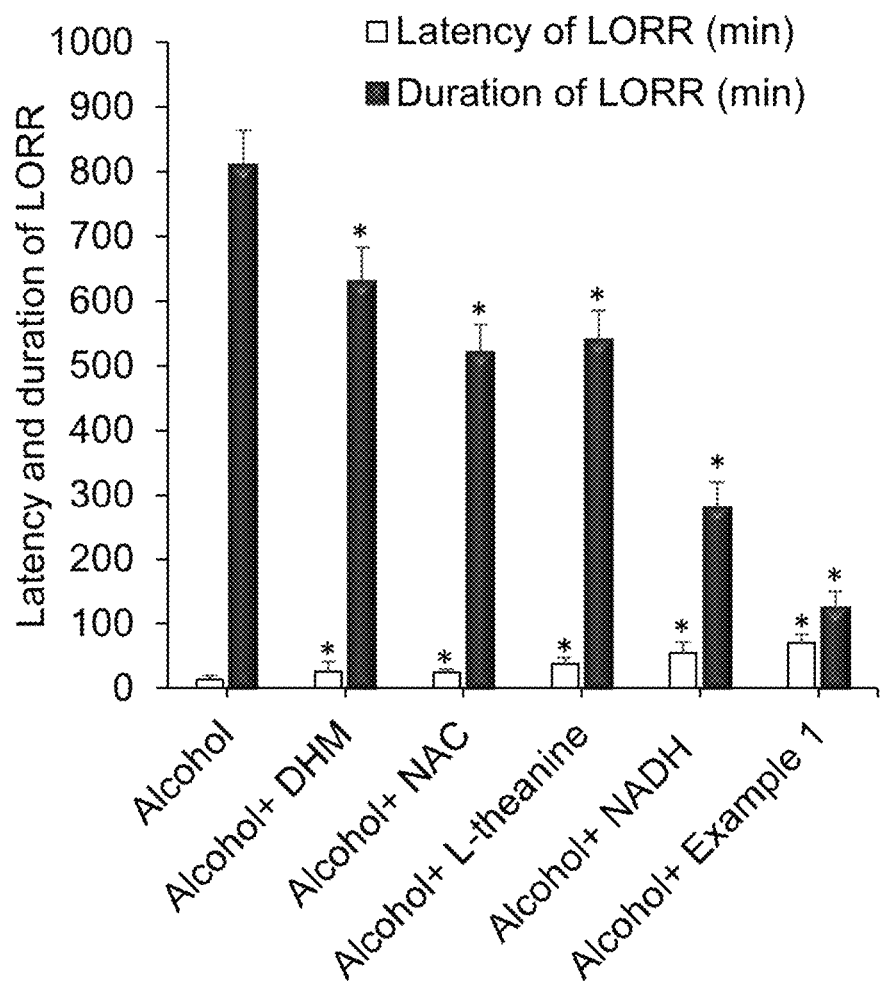
FIG. 5B a graph comparing the LORR latency and duration of male C57BL/6J mice after pre-treatment with 500 mg/kg NADH, 500 mg/kg DHM, 500 mg/kg (N-acetyl-cysteine) (NAC), 500 mg/kg L-theanine, 500 mg/kg Example 1 prior to administration of 8 ml/kg ethanol (40% w/v, in tap water) relative to male C57BL/6J mice after administration of 8 ml/kg ethanol (40% w/v, in tap water) alone.

Alcohol acts on the central nervous system, causing various behavioral problems, e.g. loss of righting reflex (LORR). Fisher's exact probability test was used to analyze the loss of righting reflex (LORR). FIG. 5A compares the LORR rate of the control group and the groups pre-treated with Example 1 or an individual active ingredient. FIG. 5B compares the LORR latency and duration of the control group and the groups pre-treated with Example 1 or an individual active ingredient. Data representing LORR latency and duration are expressed as the mean±SD (n=10). *p<0.05 vs alcohol group.

As shown in FIGS. 5A and 5B, in the model group (i.e., alcohol exposure alone), acute alcohol intake induced LORR (100% LORR rate) in all mice within an average time of 14 minutes (latency). The average length of the LORR was about 810 minutes. Administration of Example 1 and each individual ingredient can improve tolerance of the mice to acute alcohol exposure as manifested by the decrease of LORR rate (shown in FIG. 5A) and duration (FIG. 5B) as well as the prolongation of latency (FIG. 5B), and the effect of Example 1 is the most significant. Of note, less than half of the mice in the Example 1 group had a righting reflex after drinking alcohol (i.e., more than half of the mice had a loss of righting reflex), and the LORR duration was significantly shortened to 125.00 minutes, almost one sixth that of the model group. Also, the average latency increased to 70 minutes, which was 5 times that of the model group. Accordingly, these data show that administration of the active ingredient complexes according to embodiments of the present disclosure prior to alcohol exposure can dramatically improve the tolerance of mice to acute alcohol exposure.

As discussed above, treatment with active ingredient complexes according to embodiments of the present disclosure either before or after alcohol consumption can have a profound effect on various acute alcoholic liver damage and symptoms of hangover. Indeed, as discussed in more detail above, the active ingredient complexes according to embodiments of the present disclosure have protective/preventive effects when used as a pre-treatment prior to alcohol consumption, limiting the extent of acute alcoholic liver damage or the severity or onset of hangover symptoms by, e.g., reducing the alcohol (i.e., ethanol) concentration in the blood and promoting faster metabolism of ethanol to acetaldehyde, reducing hepatotoxicity due to alcohol consumption, protecting the liver from high oxidative stress caused by acute alcohol intake, and decreasing TG and VLDL levels to alleviate the abnormal lipid metabolism in acute alcoholic liver damage. And treatment with the active ingredient complexes according to embodiments of the present disclosure also improves cognitive impairment associated with alcohol intake, as discussed above with respect to the significant reductions observed in LORR onset, duration and latency. Additionally, as also discussed in more detail above, active ingredient complexes according to embodiments of the present disclosure can reduce AST and ALT levels, thereby reducing alcoholic hepatotoxicity.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" compound, "an" excipient, and the like, one or more of these components in any combination can be used according to the present disclosure.

Also, although certain embodiments have been described as "comprising" or "including" the specified components, embodiments "consisting essentially of" or "consisting of" the listed components are also within the scope of this disclosure. For example, while embodiments of the present disclosure are described as comprising a dietary supplement or pharmaceutical composition comprising an active ingredient complex and a pharmaceutically acceptable carrier, embodiments consisting essentially of or consisting of these components are also within the scope of this disclosure. Accordingly, a dietary supplement or pharmaceutical composition may consist essentially of an active ingredient complex and a pharmaceutically acceptable carrier. In this context, "consisting essentially of" means that any additional components will not materially affect the chemical, physical, therapeutic, preventive, dietary or pharmaceutical properties of the dietary supplement or pharmaceutical composition.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" compound or "an" excipient, a mixture of such materials can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples and Experiments are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. An active ingredient complex, comprising therapeutically effective amounts of:
   a) NADH (nicotinamide adenine dinucleotide (NAD)+ hydrogen (H)) or a pharmaceutically acceptable salt or derivative thereof;
   b) L-cysteine or a pharmaceutically acceptable salt or derivative thereof;
   c) Dihydromyricetin (DHM) or a pharmaceutically acceptable salt or derivative thereof;
   d) N-acetyl-cysteine (NAC) or a pharmaceutically acceptable salt or derivative thereof;
   e) L-theanine or a pharmaceutically acceptable salt or derivative thereof; and
   f) buffered vitamin C or a pharmaceutically acceptable salt or derivative thereof.

2. The active ingredient complex according to claim 1, wherein the NADH, DHM, NAC, L-Cysteine, L-theanine and Buffered Vitamin C are present in the active ingredient complex at a weight ratio of 1 (NADH):15-20 (L-Cysteine): 25-35 (DHM):5-10 (NAC):1-5 (L-theanine):1-5 (Buffered Vitamin C).

3. The active ingredient complex according to claim 1, wherein the NADH may be present in the active ingredient complex relative to one or more of the DHM, NAC, L-cysteine, L-theanine and Buffered Vitamin C at any one or more of the following weight ratios:
   1 NADH:15-20 L-Cysteine; and/or
   1 NADH:25-35 DHM; and/or
   1 NADH:5-10 NAC; and/or
   1 NADH:1-5 L-theanine; and/or
   1 NADH:1-5 Buffered Vitamin C.

4. The active ingredient complex according to claim 1, wherein:
   the NADH is present in the active ingredient complex in an amount of about 0.5 to 2.5 wt % based on a total combined weight of the NADH, L-Cysteine, DHM, NAC, L-theanine and Buffered Vitamin C; and/or
   the L-Cysteine is present in the active ingredient complex in an amount of about 20 to 40 wt % based on a total combined weight of the NADH, L-Cysteine, DHM, NAC, L-theanine and Buffered Vitamin C; and/or
   the DHM is present in the active ingredient complex in an amount of about 40 to 60 wt % based on a total combined weight of the NADH, L-Cysteine, DHM, NAC, L-theanine and Buffered Vitamin C; and/or
   the NAC is present in the active ingredient complex in an amount of about 5 to 20 wt % based on a total combined weight of the NADH, L-Cysteine, DHM, NAC, L-theanine and Buffered Vitamin C; and/or
   the L-theanine is present in the active ingredient complex in an amount of about 1 to 10 wt % based on a total combined weight of the NADH, L-Cysteine, DHM, NAC, L-theanine and Buffered Vitamin C; and/or
   the Buffered Vitamin C is present in the active ingredient complex in an amount of about 1 to 10 wt % based on a total combined weight of the NADH, L-Cysteine, DHM, NAC, L-theanine and Buffered Vitamin C.

5. A pharmaceutical composition, comprising:
   the active ingredient complex according to claim 1; and
   one or more pharmaceutically acceptable carriers, excipients, adjuvants and/or diluents.

6. The pharmaceutical composition according to claim 5, wherein the pharmaceutical composition comprises a tablet, capsule or powder.

7. A dietary supplement composition, comprising:
   the active ingredient complex according to claim 1; and
   one or more pharmaceutically acceptable carriers, excipients, adjuvants and/or diluents.

8. The dietary supplement composition according to claim 7, wherein the dietary supplement composition comprises a tablet, capsule or powder.

9. A method of treating, reducing the likelihood of developing, reducing the severity of, or ameliorating acute alcoholic liver damage in a subject in need thereof, the method comprising administering to the subject a therapeutically effective amount of the active ingredient complex according to claim 1.

10. The method according to claim 9, wherein the administration of the active ingredient complex comprises administering the active ingredient complex prior to the subject consuming or being exposed to alcohol.

11. The method according to claim 9, wherein the administration of the active ingredient complex comprises orally administering to the subject a dietary supplement comprising the active ingredient complex.

12. The method according to claim 11, wherein the administration of the active ingredient complex comprises administering a dose of the active ingredient complex of about 0.01 mg/kg to about 50 mg/kg per day.

13. A method of increasing the tolerance to alcohol in a subject in need thereof, the method comprising administering to the subject a therapeutically effective amount of the active ingredient complex according to claim 1.

14. The method according to claim 13, wherein the administration of the active ingredient complex comprises administering the active ingredient complex prior to the subject consuming or being exposed to alcohol.

15. The method according to claim 13, wherein the administration of the active ingredient complex comprises orally administering to the subject a dietary supplement comprising the active ingredient complex.

16. The method according to claim 15, wherein the administration of the active ingredient complex comprises administering a dose of the active ingredient complex of about 0.01 mg/kg to about 50 mg/kg per day.

17. A method of treating, reducing the likelihood of developing, reducing the severity of, or alleviating the symptoms of an alcohol hangover in a subject in need thereof, the method comprising administering to the subject a therapeutically effective amount of the active ingredient complex according to claim 1.

18. The method according to claim 17, wherein the administration of the active ingredient complex comprises administering the active ingredient complex prior to the subject consuming or being exposed to alcohol.

19. The method according to claim 17, wherein the administration of the active ingredient complex comprises orally administering to the subject a dietary supplement comprising the active ingredient complex.

20. The method according to claim 19, wherein the administration of the active ingredient complex comprises administering a dose of the active ingredient complex of about 0.01 mg/kg to about 50 mg/kg per day.

* * * * *